United States Patent
Yamamoto

(10) Patent No.: US 10,524,763 B2
(45) Date of Patent: Jan. 7, 2020

(54) ULTRASOUND INSPECTION DEVICE, ULTRASOUND IMAGE DATA GENERATION METHOD, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 793 days.

(21) Appl. No.: 14/670,142

(22) Filed: Mar. 26, 2015

(65) Prior Publication Data

US 2015/0196273 A1 Jul. 16, 2015

Related U.S. Application Data

(63) Continuation of application No. PCT/JP2013/075906, filed on Sep. 25, 2013.

(30) Foreign Application Priority Data

Sep. 27, 2012 (JP) .................................. 2012-214409

(51) Int. Cl.
*A61B 8/14* (2006.01)
*A61B 8/08* (2006.01)
*A61B 8/00* (2006.01)

(52) U.S. Cl.
CPC .............. *A61B 8/14* (2013.01); *A61B 8/5207* (2013.01); *A61B 8/4488* (2013.01)

(58) Field of Classification Search
CPC ... A61B 8/5261; A61B 8/4245; A61B 8/0825; A61B 8/4416; A61B 8/485; A61B 8/58;
(Continued)

(56) References Cited

U.S. PATENT DOCUMENTS 6,551,246 B1 * 4/2003 Ustuner .............. G01S 7/52026
600/447
8,485,977 B2 7/2013 Hirama
(Continued)

FOREIGN PATENT DOCUMENTS

JP         09-224938 A  *  9/1997   .............. A61B 8/00
JP       2009-240700 A     10/2009

OTHER PUBLICATIONS

Sohn et al. 2011 Electronics Letters 47:89-91.*
(Continued)

*Primary Examiner* — Baisakhi Roy
*Assistant Examiner* — Patrick M Mehl
(74) *Attorney, Agent, or Firm* — Birch, Stewart, Kolasch & Birch, LLP

(57) ABSTRACT

The present invention provides an ultrasound inspection device, an ultrasound image data generation method, and a computer-readable recording medium in which is stored a program, which determine for each of data calculation points whether or not the distance to a transmission focal point is with a predetermined range, and when the distance from the data calculation point to the transmission focal point is outside the predetermined range, superimposition of a plurality of first element data is carried out assuming an ultrasonic beam to be a convergent wave, and when the distance from the data calculation point to the transmission focal point is within the predetermined range, the superimposition of the plurality of first element data is carried out assuming an ultrasonic beam to be a planar wave to thereby generate second element data corresponding to the data calculation points.

17 Claims, 8 Drawing Sheets

(58) Field of Classification Search
CPC ... A61B 8/00; G01S 7/52049; G01S 15/8915;
G10K 11/346
See application file for complete search history.

(56) References Cited

U.S. PATENT DOCUMENTS

| | | | | |
|---|---|---|---|---|
| 2009/0326377 | A1* | 12/2009 | Hirama | G01S 7/52046 600/447 |
| 2010/0076312 | A1* | 3/2010 | Katsuyama | A61B 8/00 600/443 |
| 2011/0077518 | A1* | 3/2011 | Miyachi | A61B 5/02007 600/443 |
| 2012/0179044 | A1* | 7/2012 | Chiang | A61B 8/0883 600/447 |

OTHER PUBLICATIONS

International Preliminary Report on Patentability and English translation of the Written Opinion of the International Searching Authority (Forms PCT/IB/338, PCT/IB/373 and PCT/ISA/237), dated Apr. 9, 2015, for International Application No. PCT/JP2013/075906.
International Search Report, issued in PCT/JP2013/075906, dated Nov. 5, 2013.

\* cited by examiner

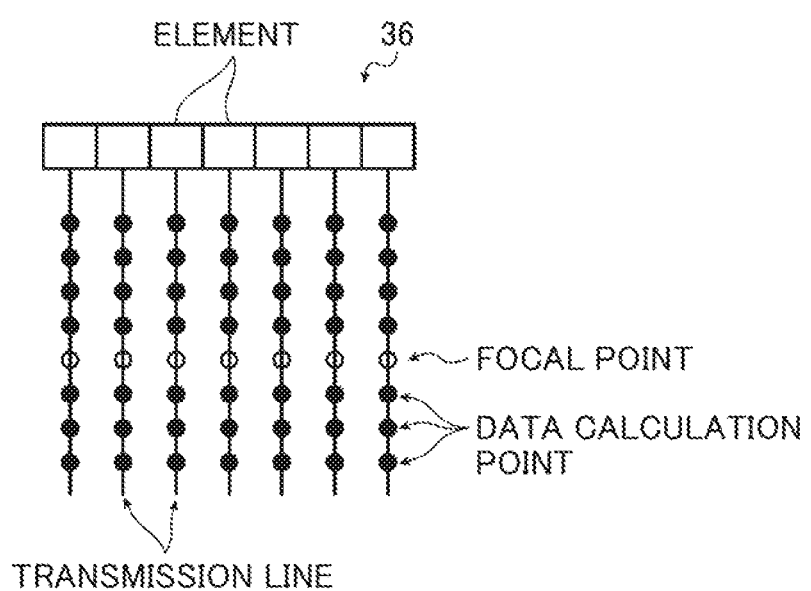

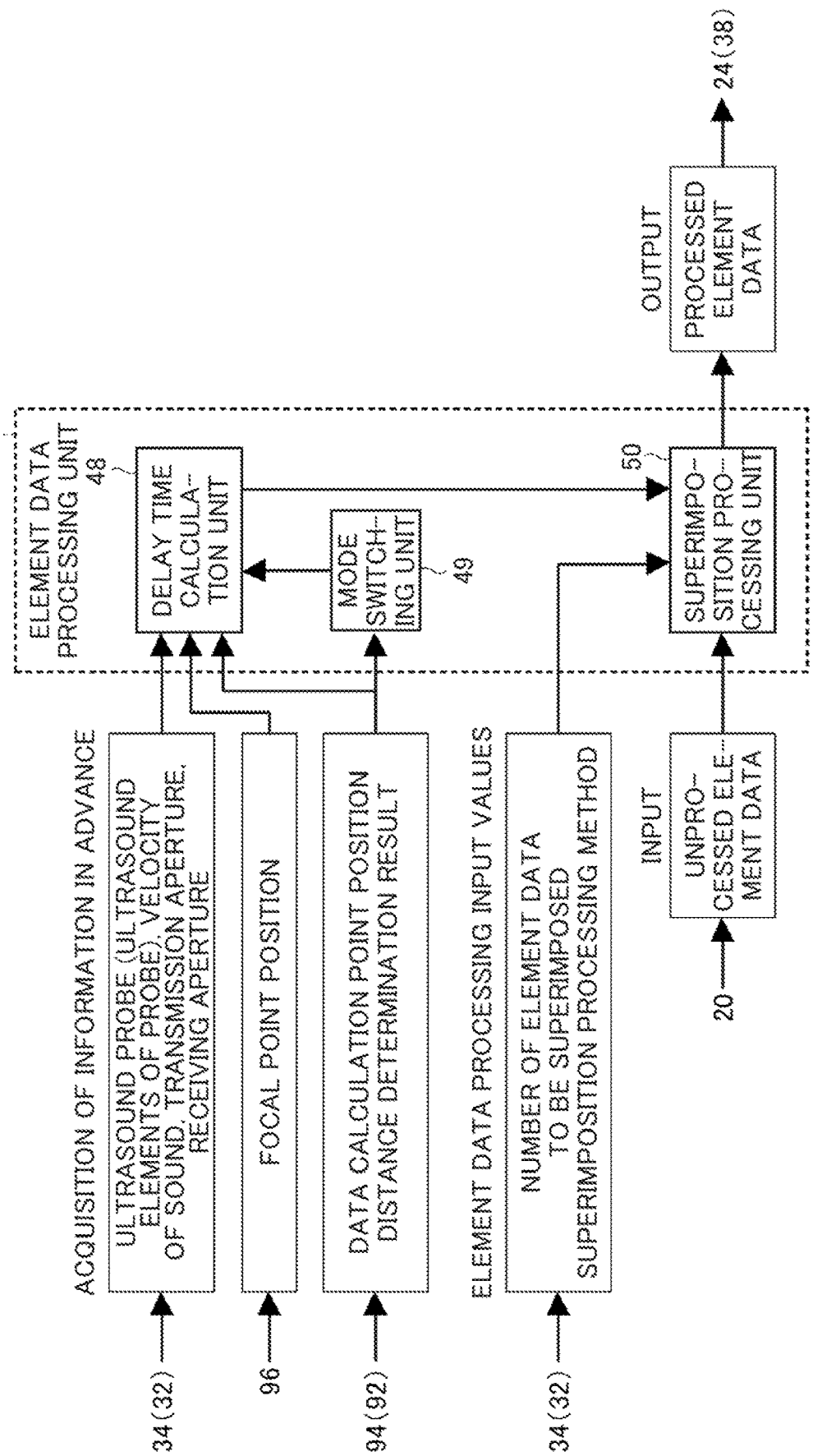

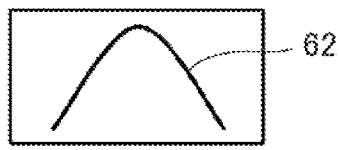
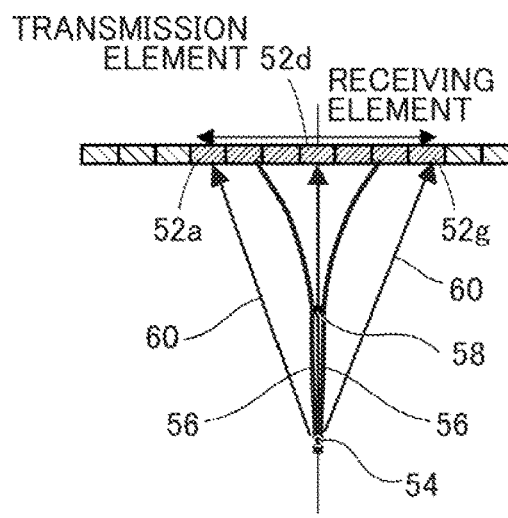
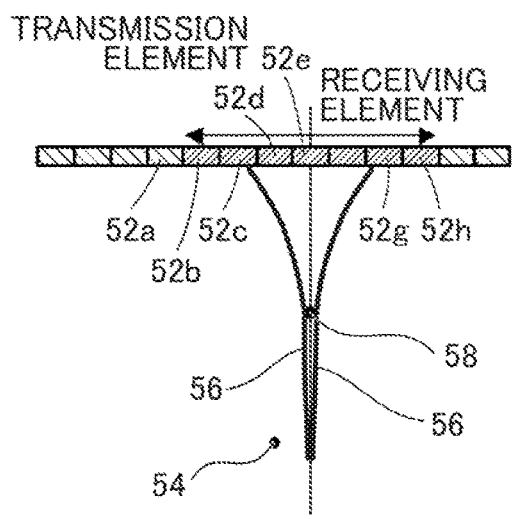
FIG. 4A
FIG. 4C
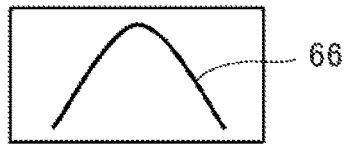
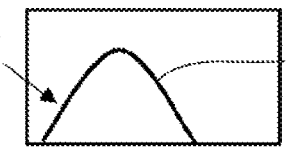
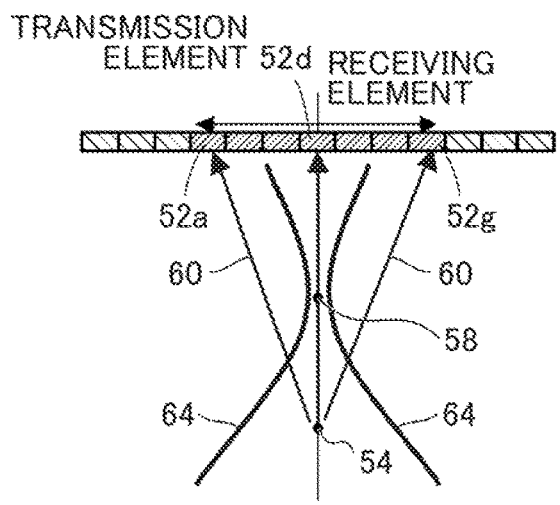
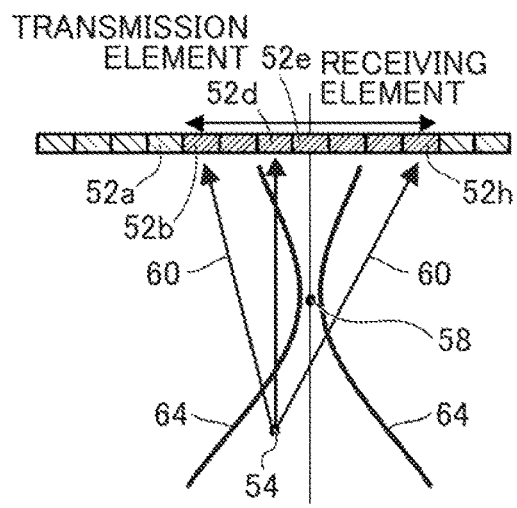
FIG. 5A
FIG. 5C

ULTRASOUND INSPECTION DEVICE, ULTRASOUND IMAGE DATA GENERATION METHOD, AND RECORDING MEDIUM

CROSS-REFERENCE TO RELATED APPLICATIONS

This application is a Continuation of PCT International Application No. PCT/JP2013/075906 filed on Sep. 25, 2013, which claims priority under 35 U.S.C. § 119(a) to Japanese Application No. 2012-214409 filed on Sep. 27, 2012. Each of the above application(s) is hereby expressly incorporated by reference, in its entirety, into the present application.

BACKGROUND OF THE INVENTION

The present invention relates to an ultrasound inspection device, an ultrasound image data generation method, and a recording medium in which is stored a program, which capture an image of an object to be inspected, such as an organ within the body or the like by transmitting and receiving an ultrasonic beam, to generate an ultrasound image used for examining and diagnosing the object to be inspected.

Conventionally, ultrasound inspection devices such as ultrasound imaging and diagnostic devices using ultrasound images are used in the medical field. Normally this type of ultrasound inspection device includes an ultrasound probe that contains a plurality of elements (ultrasound transducers), and a device body connected to the ultrasound probe, the plurality of elements of the ultrasound probe transmits an ultrasonic beam towards the object to be inspected (inspection object), and receives the echoes of the ultrasonic wave from the inspection object at the ultrasound probe, and by electrically processing the received ultrasonic echo signals in the device body, an ultrasound image is generated.

In an ultrasound inspection device, when generating an ultrasound image, the ultrasonic beam is transmitted with the focal points of the plurality of elements of the probe focused on the area to be examined in the inspection object, for example, an organ within the body or a lesion within that organ or the like, and the ultrasonic echoes from reflectors in the inspection object, for example the surface or boundary of the organ or lesion or the like, are received by the plurality of elements, but the ultrasonic echoes reflected from the same reflector are received by the plurality of elements, so the ultrasonic echo signals reflected by a reflector located at the focal position of the ultrasonic beam transmitted from the transmitting element and received by an element that is different from the transmitting element may be delayed with respect to the ultrasonic echo signal received by the transmitting element, so after the ultrasonic echo signals received by the plurality of elements are subject to analog to digital (A/D) conversion to become element data, receiving focus processing is carried out on the element data, in other words sonic signals are generated by correcting delays and phase addition is carried out to align the phases, and the ultrasound image is generated based on these obtained sonic signals.

In this ultrasound inspection technology, in order to improve the image quality of the ultrasound images, the signal quality is improved compared with the conventional technology by adding signals transmitted with a plurality of different focal points.

For example, in JP 2009-240700 A, a virtual point sound source is formed by focusing a transmitted ultrasonic wave emitted from a plurality of vibration elements that compose a transmission vibration element group onto a transmission focal point, then, the received ultrasonic waves reflected from a plurality of continuous measurement points as a result of the transmission ultrasonic wave emitted from this point sound source are received by a plurality of vibration elements that compose a receiving vibration element group, and phase addition is carried out on the reception signals for the channels obtained to form the receiving focusing point of the measurement point. In addition, an ultrasound diagnostic device is disclosed that carries out transmission phase addition in which the same phase addition is carried out on reception signals obtained using each transmission element group that has been successively shifted in the direction of the array of the vibration elements of the transmission vibration element group, and corrects the transmission delay time caused by the difference in each propagation distance from the transmission focal point to the measurement point for the reception signals after this receiving phase addition.

In JP 2009-240700 A, it is possible to form a transmission beam and receiving beam having a virtually uniform fine beam width in the depth direction of the inspection object with high accuracy and high sensitivity, by carrying out the receiving phase addition and the transmission phase addition on the reception signals obtained from the plurality of vibration elements. Therefore, JP 2009-240700 A discloses how to generate and display image data with excellent spatial resolution, contrast resolution, and S/N ratio (signal-noise ratio).

SUMMARY OF THE INVENTION

However, in the technology disclosed in JP 2009-240700 A, an image can be obtained with higher image quality than with conventional technology, but to produce one line of data it is necessary to generate a plurality of transmission beams while changing the transmission position, so the number of transmissions is increased and the frame rate is reduced compared with conventional technology, which has the problem that its properties in real time are poor. Also, in JP 2009-240700 A, the focal point is regarded as a virtual point sound source, and a plurality of reception signals is synthesized, but in reality the focal point is not focused enough to be considered to be a point sound source, and it has a finite width, so the closer the image region is to the focal point, the lower the accuracy of the data when synthesizing the reception signals, which has the problem that the SN ratio and the resolution are reduced.

It is an object of the present invention to provide an ultrasound inspection device, an ultrasound image data generation method, and a recording medium in which is stored a program capable of solving the above problems with the conventional technology, that increases the SN ratio and the resolution of the whole image, including the region near the focal point, and, enables a sharp ultrasound image to be obtained having high resolution and ideal spatial resolution, with a frame rate that is unchanged from that of the conventional technology.

In order to achieve the aforementioned object, the present invention provides an ultrasound inspection device for inspecting an object to be inspected using an ultrasonic beam, comprising:

a focal point setting unit for setting a plurality of transmission focal points within the object to be inspected;

a probe including a plurality of elements, the plurality of elements generating each of the components of the ultrasonic beam and receiving ultrasonic echoes reflected by the object to be inspected and outputting received analog element signals;

a transmitter for causing the probe to generate the ultrasonic beam towards each of the transmission focal points set by the focal point setting unit, using the plurality of elements;

a receiver for receiving the analog element signals received by the plurality of elements corresponding to transmission of each of the ultrasonic beams towards each of the transmission focal points, and performing predetermined processing;

an A/D converter for carrying out A/D conversion on analog element signals processed by the receiver, to produce first element data being digital element signals;

a calculation point setting unit for setting at least one data calculation point within the object to be inspected;

a calculation point positional determination unit for determining for each of the data calculation points set by the calculation point setting unit whether or not the distance to the transmission focal point is equal to or less than a predetermined threshold; and an element data processing unit for superimposing the first element data obtained from the transmission of the plurality of ultrasonic beams, and generating second element data corresponding to the data calculation points; wherein the element data processing unit includes a first mode that carries out superimposition of the plurality of first element data assuming the ultrasonic beam to be a convergent wave, and, a second mode that carries out superimposition of the plurality of first element data assuming the ultrasonic beam to be a planar wave, and when the distance from the data calculation point to the transmission focal point is greater than the predetermined threshold, the superimposition of the plurality of first element data is carried out in the first mode, and when the distance from the data calculation point to the transmission focal point is equal to or less than the predetermined threshold, the superimposition of the plurality of first element data is carried out in the second mode.

In the ultrasound inspection device, it is preferable that the calculation point setting unit sets the data calculation point on a transmission line of the ultrasonic beam, and the calculation point positional determination unit determines based on the distance to the transmission focal point on the transmission line corresponding to the data calculation point.

It is also preferable that the transmitter causes the probe to transmit the ultrasonic beam using the plurality of elements in accordance with each of the transmission focal points by changing an element in the center.

It is also preferable that the receiver changes an element in the center of the plurality of elements, the plurality of elements receiving the ultrasonic echoes corresponding to the transmission of the ultrasonic beam by the transmitter.

It is also preferable that the receiver causes the same elements as the plurality of elements used for transmitting the ultrasonic beam by the transmitter to receive the ultrasonic echoes.

It is also preferable that the element data processing unit superimposes the plurality of first element data in accordance with the time the elements received the ultrasonic echoes and the positions of the elements, to generate the second element data corresponding to the data calculation points.

It is also preferable that the element data processing unit includes a delay time calculation unit calculating a delay time for the two or more first element data, and a superimposition processing unit carrying out superimposition of the two or more first element data based on the delay times calculated and the positions of the receiving elements of the probe, to generate the second element data, and the delay time calculation unit calculates the delay time assuming the ultrasonic beam to be a convergent wave in the case of the first mode, and calculates the delay time assuming the ultrasonic beam to be a planar wave in the case of the second mode.

It is also preferable that the delay time calculation unit calculates the delay time in the first mode when the distance from the data calculation point to the transmission focal point is equal to or greater than a predetermined first threshold, calculates the delay time in the second mode when the distance from the data calculation point to the transmission focal point is equal to or smaller than a second threshold, the second threshold being smaller than the first threshold, and when the distance from the data calculation point to the transmission focal point is between the first threshold and the second threshold, the delay time is calculated from an average weighted in accordance with the distance to the transmission focal point of the delay time calculated assuming the ultrasonic beam to be a convergent wave and the delay time calculated assuming the ultrasonic beam to be a planar wave.

It is also preferable that the delay time calculation unit calculates the delay time of the two or more first element data based on at least one of information obtained in advance regarding the probe, a velocity of sound in the object to be inspected, a position of the transmission focal point of the ultrasonic beam, a transmission aperture of the probe of the transmitter, and a receiving aperture of the probe of the receiver, and the superimposition processing unit generates the second element data by superimposing the two or more first element data based on a number of first element data to be superimposed from among the two or more first element data and a superimposition processing method, the number of the first element data and the method being set in advance.

It is also preferable that the element data processing unit uses the first element data obtained from transmission of the plurality of ultrasonic beams with different elements in the center.

It is also preferable that the element data processing unit generates the second element data using the first element data obtained from transmission of the plurality of ultrasonic beams with overlapping transmission regions of the ultrasonic beams.

It is also preferable that the element data processing unit superimposes the plurality of first element data obtained from transmission of ultrasonic beams with each element being continuous in a direction of an array of the elements as the element in the center, to generate the second element data.

It is also preferable that the element data processing unit superimposes the plurality of first element data obtained from transmission of ultrasonic beams with the same number of elements on either side of an element in the center as a respective element in the center when transmitting the ultrasonic beam corresponding to the data calculation point, to generate the second element data corresponding to the data calculation point.

It is also preferable that the element data processing unit superimposes the two or more first element data after applying a weighting coefficient to each of the first element data.

It is also preferable for the ultrasound inspection device to further include an element data storage unit storing all the first element data output by the receiver.

In order to achieve the aforementioned object, the present invention further provides an ultrasound image data generation method for generating an ultrasonic beam, inspecting an object to be inspected, and generating ultrasound image data with a probe, the probe including a plurality of elements, the plurality of elements generating each components of the ultrasonic beam, receiving ultrasonic echoes reflected by the object to be inspected, and outputting the received analog signals, the method comprising:

a focal point setting step of setting a plurality of transmission focal points within the object to be inspected;

a transmission step of causing the probe to generate the ultrasonic beam towards each of the transmission focal points set in the focal point setting step, using the plurality of elements;

a receiving step of receiving the analog element signals received by the plurality of elements corresponding to the transmission of each of the ultrasonic beams towards each of the transmission focal points to perform predetermined processing;

an A/D conversion step of carrying out A/D conversion on the analog element signals processed in the receiving step, to produce first element data being digital element signals;

a calculation point setting step of setting at least one data calculation point within the object to be inspected;

a calculation point positional determination step of determining for each of the data calculation points set in the calculation point setting step whether or not a distance to the transmission focal point is within a predetermined range; and an element data processing step of superimposing the first element data obtained from the transmission of the plurality of ultrasonic beams, to generate second element data corresponding to the data calculation point; wherein the element data processing step includes a first mode carrying out superimposition of the plurality of first element data assuming the ultrasonic beam to be a convergent wave, and, a second mode carrying out superimposition of the plurality of first element data assuming the ultrasonic beam to be a planar wave, and when the distance from the data calculation point to the transmission focal point is greater than a predetermined threshold, the superimposition of the plurality of first element data is carried out in the first mode, and when the distance from the data calculation point to the transmission focal point is equal to or less than the predetermined threshold, the superimposition of the plurality of first elements data is carried out in the second mode.

In order to achieve the aforementioned object, the present invention further provides a computer-readable recording medium in which is stored an ultrasound image data generation program for causing a computer to execute: generating an ultrasonic beam, inspecting an object to be inspected, and generating ultrasound image data with a probe including a plurality of elements; the plurality of elements generating each components of the ultrasonic beam, receiving ultrasonic echoes reflected by the object to be inspected, and outputting the received analog signals, the program comprising:

a focal point setting step of setting a plurality of transmission focal points within the object to be inspected;

a transmission stop of causing the probe to generate the ultrasonic beam towards each of the transmission focal points set in the focal point setting step, using the plurality of elements;

a receiving step of receiving the analog element signals received by the plurality of elements corresponding to the transmission of each of the ultrasonic beams towards each of the transmission focal points to perform predetermined processing;

an A/D conversion step of carrying out A/D conversion on the analog element signals processed in the receiving step, to produce first element data being digital element signals;

a calculation point setting step of setting at least one data calculation point within the object to be inspected;

a calculation point positional determination step of determining for each of the data calculation points set in the calculation point setting step whether or not a distance to the transmission focal point is within a predetermined range; and an element data processing step of superimposing the first element data obtained from the transmission of the plurality of ultrasonic beams, to generate second element data corresponding to the data calculation point; wherein the element data processing step includes a first mode carrying out superimposition of the plurality of first element data assuming the ultrasonic beam to be a convergent wave, and, a second mode carrying out superimposition of the plurality of first element data assuming the ultrasonic beam to be a planar wave, and when the distance from the data calculation point to the transmission focal point is greater than a predetermined threshold, the superimposition of the plurality of first element data is carried out in the first mode, and when the distance from the data calculation point to the transmission focal point is equal to or less than the predetermined threshold, the superimposition of the plurality of first elements data is carried out in the second mode.

According to the present invention, the modes when superimposing the element data include a mode that assumes the ultrasonic beam to be a convergent wave, and a mode that assumes the ultrasonic beam to be a planar wave, and the mode is switched in accordance with the position of the focal point, so it is possible to increase the SN ratio and the resolution of the image as a whole, without a reduction in the accuracy of the element data in regions where the accuracy of the data is reduced by superimposition of the element data as a convergent wave, such as near the focal point, and, it is possible to obtain sharp ultrasound images having high resolution and ideal spatial resolution, with a frame rate that is no different from that of conventional technology.

BRIEF DESCRIPTION OF THE DRAWINGS

FIG. 2 is a schematic explanatory view of the focal point positions and data calculation points.

FIG. 3 is a block diagram schematically showing an example of the configuration of an element data processing unit of the ultrasound inspection device of FIG. 1.

FIGS. 4A and 4C are explanatory views of cases where ideal ultrasonic beams are transmitted from an element directly above the reflection point of the inspection object and from an element not directly above respectively, and FIGS. 4B and 4D are the element data obtained respectively.

FIGS. 5A and 5C are explanatory views of cases where actual ultrasonic beams are transmitted from an element directly above the reflection point of the inspection object and from an element not directly above respectively, and FIGS. 5B and 5D are the element data obtained respectively.

DETAILED DESCRIPTION OF THE INVENTION

The following is a detailed description of the ultrasound inspection device, the ultrasound image data generation method, and the computer-readable recording medium in which is stored the program according to the present invention based on the preferred embodiments shown on the accompanying drawings.

Figure 1:
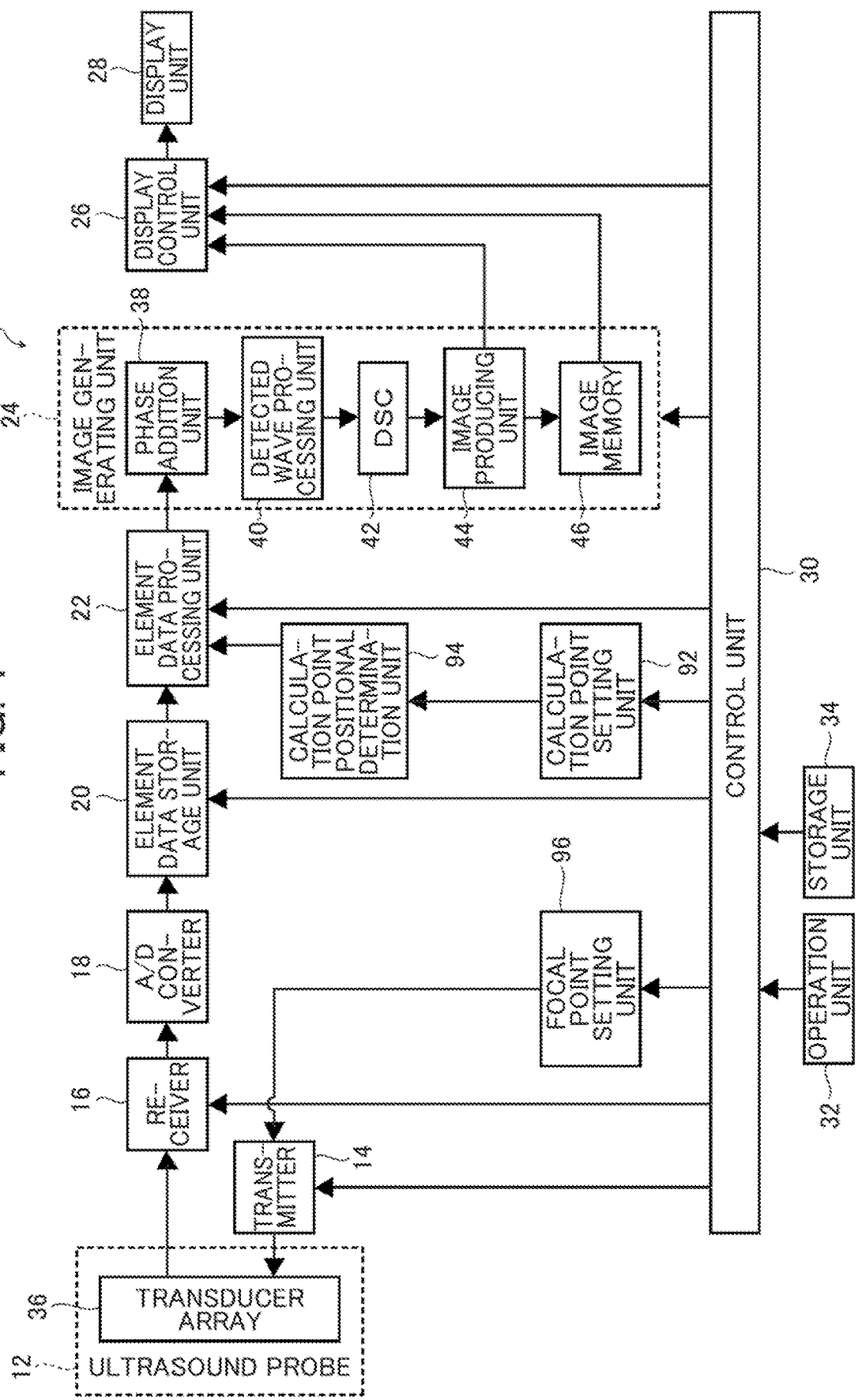
FIG. 1 is a block diagram schematically showing an example of the configuration of an ultrasound inspection device according to the present invention.

FIG. 1 is a block diagram schematically showing an embodiment of the configuration of an ultrasound inspection device according to the present invention.

As shown in FIG. 1, an ultrasound inspection device 10 includes an ultrasound probe 12, a transmitter 14 and receiver 16 connected to the ultrasound probe 12, an A/D converter 18, an element data storage unit 20, an element data processing unit 22, an image generating unit 74, a display control unit 26, a display unit 28, a control unit 30, an operation unit 32, a storage unit 34, a calculation point setting unit 92, a calculation point positional determination unit 94, and a focal point setting unit 96.

The ultrasound probe 12 includes a transducer array 36 as used in a normal ultrasound inspection device.

The transducer array 36 includes a plurality of elements, namely ultrasound transducers, arranged in a one-dimensional or two-dimensional array. When capturing an ultrasound image of an object to be inspected (hereafter referred to as inspection object), the ultrasound transducers transmit an ultrasonic beam to the inspection object in accordance with a drive signal received from the transmitter 14, and receive ultrasonic echoes from the inspection object and output a reception signal (analog element signal). In the present embodiment, each of a predetermined number of ultrasound transducers forming one group within the plurality of ultrasound transducers of the transducer array 36 generates each of the components of a single ultrasonic beam, and a set of a predetermined number of ultrasound transducers generates a single ultrasonic beam that is transmitted to the inspection object.

Each ultrasound transducer comprises an element, namely a transducer, with an electrode formed at both ends of a piezoelectric material such as, for example, a piezoelectric ceramic as represented by lead zirconate titanate (PZT), a polymer piezoelectric element as represented by polyvinylidene fluoride (PVDF), and a piezoelectric single crystal as represented by lead magnesium niobate-lead titanate (PMN-PT).

When a voltage in pulse form or in the form of a continuous wave is applied to the electrodes of this type of transducer, the piezoelectric material is constricted, and an ultrasonic wave in pulse form or continuous wave form is generated from each transducer, and an ultrasonic beam is formed by the synthesis of these ultrasonic waves. Also, each of the transducers is constricted by receiving the transmitted ultrasonic waves and generates an electrical signal, and the electrical signals are output as ultrasound reception signals (analog element signals).

The focal point setting unit 96 sets a plurality of transmission lines, and, the focal point position on each transmission line, in accordance with transmission focal point information (information on the position of the focal point) input from the operation unit 32, when the transducer array 36 transmits the ultrasonic beam.

Specifically, the focal point setting unit 96 sets a plurality of transmission lines for transmitting ultrasonic beams, in accordance with settings such as the display region (examination region) and depth input from the operation unit 32, and information regarding the arrangement spacing of the transducers of the transducer array 36, and the like, and automatically sets the positions that will become the focal points of the ultrasonic beams on each transmission line, in the same way as for a conventional ultrasound inspection device.

Note that the focal point setting unit 96 may set the focal point positions from information on the position of the focal points directly input by an operator from the operation unit 32.

FIG. 2 shows an example of set focal point positions.

In the example shown in FIG. 2, a single transmission line is set corresponding to each element (ultrasound transducer) of the transducer array 36, and collinear with each element. Also, a single focal point position is set on each transmission line at the same depth.

The information on the set focal point positions is supplied to the transmitter 14, the calculation point positional determination unit 94, and the control unit 30.

The transmitter 14 includes, for example, a plurality of pulsers, that forms a single ultrasonic beam from the ultrasonic beam components transmitted from the group of the predetermined number of ultrasound transducers (hereafter referred to as ultrasound elements) of the transducer array 36, based on a selected transmission delay pattern in accordance with a control signal from the control unit 30 and the information on the position of the focal point from the focal point setting unit 96, and adjusts the amount of delay of each drive signal so as to form the focal point at the set focal point position, and supplies them to the plurality of ultrasound elements that form the group.

Specifically, the transmitter 14 supplies drive signals so that an ultrasonic beam forming a focal point at the set focal point position is transmitted with an ultrasound element collinear with the set transmission line as the central element, and a plurality of ultrasound elements that includes the central element and a plurality of ultrasound elements on both sides thereof as the group of transmission elements (transmission aperture).

The ultrasonic echoes generated by interaction between the inspection object and the ultrasonic beam transmitted from the transducer array 36 in accordance with control signals from the control unit 30 are received by the transducer array 36 and output to the receiver 16 which amplifies and outputs the reception signals, in other words the analog element signal for each ultrasound element.

Specifically, as a group of receiving elements (receiving aperture) that includes the central element when the corresponding ultrasonic beam was transmitted, and a plurality of ultrasound elements on both sides of the central element, the receiver 16 receives echoes reflected within the inspection object.

Here the receiver 16 outputs as single analog element data (first element data) the plurality of analog element signals received by the plurality of ultrasound elements corresponding to a single transmission of a ultrasonic beam, including information on the receiving ultrasound elements and information on the time received. In other words, the element data (first element data) is data that represents the strength of the reception signal with respect to the element position and time received (see FIG. 4B).

Also, the receiver 16 receives ultrasonic echoes and outputs analog element data for each ultrasonic beam transmitted by the transmitter 14. Therefore, when the transmitter 14 transmits a plurality of ultrasonic beams in accordance with the set transmission lines and focal point positions, a plurality of analog element data is output corresponding to each transmission.

The receiver 16 supplies the analog element data to the A/D converter 18.

The A/D converter 18 is connected to the receiver 16, and converts the analog element data supplied from the receiver 16 into digital element data (first element data). The A/D converter 18 supplies the A/D converted digital element data to the element data storage unit 20.

The element data storage unit 20 stores the digital element data output from the A/D converter 18 in sequence. Also, the element data storage unit 20 stores information regarding the frame rate input from the control unit 30 (for example, parameters indicating the depth of the ultrasonic wave reflection position, density of the scan lines, width of the field of view) in association with the above digital element data (hereafter simply referred to as element data). Here, the element data storage unit 20 stores and retains two or more element data obtained by transmitting and receiving ultrasonic waves on mutually different transmission lines, based on control by the control unit 30.

The calculation point setting unit 92 sets the positions of a plurality of data calculation points for processing element data by the element data processing unit 22 which is described later, based on image capturing conditions input from the operation unit 32.

Specifically, the calculation point setting unit 92 sets a plurality of data calculation points (sampling points) for processing of element data on each transmission line, based on settings such as the display region (scan region) input from the operation unit 32, the depth, and the image quality, and, information on the transmission lines and focal point positions set by the focal point setting unit 96, and information regarding the arrangement spacing of the transducers of the transducer array 36, and the like.

FIG. 2 shows an example of the set sampling points.

In the example shown in FIG. 2, a transmission line is set on each element of the transducer array 36, and on each transmission line a plurality of sampling points is arranged at equal intervals. Note that sampling points are also set at the focal point positions.

In the example on the drawing the sampling points are arranged at equal spacing, but this is not a limitation, and the spacing of the sampling points may be varied in accordance with the depth. For example, the spacing of the sampling points may be reduced in the depth region of interest.

The set sampling point positional information is supplied to the calculation point positional determination unit 94.

The calculation point positional determination unit 94 is a unit that determines whether or not the focal point and distance of each of the sampling points (data calculation points) set by the calculation point setting unit 92 are within predetermined ranges.

Specifically, the calculation point positional determination unit 94 calculates the distance to the focal point on the same transmission line for each of the sampling points set by the calculation point setting unit 92, and determines whether or not the calculated distance is within a predetermined threshold, in other words whether or not the sampling point is close to the focal point.

There is no particular limitation to the value of the threshold for determining the distance to the focal point, but it may be set in accordance with transmission conditions such as the number of the apertures and the F-value which change the convergence of the focal point, and for example is in the range 5 to 30 mm. In addition, if the F-value is small and the convergence of the focal point is large, it may be narrowed down and set within the range of about 5 mm, and conversely if the F-value is large and the convergence is low, it may be set wider within the range of about 30 mm. Also, the thresholds may be changed from the operation unit 32.

Also, in the example in the drawings, a single focal point is configured to be set on a single transmission line, but this is not a limitation, and a plurality of focal points may be set on a single transmission line, and if a plurality of focal points is set on a single transmission line, it may be determined whether or not the distance to the closest focal point is within the predetermined threshold.

Also, in the example shown in the drawings, the depth of the set focal points is the same on all transmission lines, but this is not a limitation, and the focal points may be set to different depths on each transmission line. Also, in this case, there is no limitation to it being a configuration in which it is determined whether or not the distance to the focal point on the same transmission line is within the threshold, and it may be determined whether or not the distance to the closest focal point including different transmission lines is within the threshold.

The calculation point positional determination unit 94 supplies the determination results to the element data processing unit 22.

Based on the control of the control unit 30, the element data processing unit 22 reads from the element data storage unit 20 the element data obtained by transmitting the ultrasonic beam to the transmission line on which the focal point exists (hereafter referred to as unprocessed element data) and the element data corresponding to a transmission line that is different from this element data (unprocessed element data), and based on the information on time received and information on the geometric arrangement of the ultrasound elements, the times and positions are corrected and superimposed, to generate element data after superimposition processing (second element data, hereafter referred to as processed element data), thereby producing element data corresponding to this sampling point. In other words, the element data processing unit 22 carries out processing to superimpose the unprocessed element data, and reconstructs the element data corresponding to this sampling point.

Here, the element data processing unit 22 has a first mode that assumes the ultrasonic beam to be a convergent wave and calculates the deviation in the time received between superimposed unprocessed element data (time delay), and a second mode that assumes the ultrasonic beam to be a planar wave and calculates the time delay between superimposed unprocessed element data, and in accordance with the determination result of the calculation point positional determination unit 94, when the sampling point is far from the focal point, the delay time is calculated in the first mode, and when the sampling point is near the focal point, the delay time is calculated in the second mode, and the unprocessed element data is superimposed to generate the processed element data.

The element data processing unit 22 supplies the processed element data for each sampling point to the image generating unit 24 (phase addition unit 38).

As stated above, in order to obtain high-quality images, if a plurality of transmission beams is generated while changing the transmission position in order to produce data for one line, the number of transmissions is increased so the frame rate is reduced, which has the problem that the real-time properties become poorer. Also, if a plurality of reception signals is synthesized by considering the focal point to be a virtual point sound source, in reality the focal point is not converged sufficiently that it can be considered to be a point sound source, and it has a finite spread, so at the regions near the focal point, the data accuracy is reduced when synthesizing the reception signal, which has the problem that the SN ratio or the resolution is reduced.

In contrast, the present invention is switched between the first mode that superimposes the element data assuming the ultrasonic beam to be a convergent beam, and the second mode that superimposes the element data assuming the ultrasonic beam to be a planar wave, depending on whether the distance between the data calculation point and the focal point is within the predetermined range or not, and the first element data is superimposed to generate the second element data.

In this way, it is possible to superimpose the element data with good accuracy, for positions both far from and near to the focal point, so it is possible to increase the SN ratio and increase the resolution over the whole image, and, it is possible to obtain sharp ultrasound images having the ideal spatial resolution and high resolution, with frame rate the same as for conventional technology.

The element data processing unit 22 is described in detail later.

Under the control of the control unit 30, the image generating unit 24 generates sonic ray signals (received data) from the element data supplied from the element data processing unit 22, and generates the ultrasound image from the sonic ray signals.

The image generating unit 24 includes the phase addition unit 38, a detected wave processing unit 40, a DSC 42, an image producing unit 44, and an image memory 46.

The phase addition unit 38 selects one receiving delay pattern from among a plurality of receiving delay patterns that are stored in advance, in accordance with a receiving direction set in the control unit 30, and based on the selected receiving delay pattern, applies and adds a delay to each of the signals for each element of the elements data, to carry out receiving focus processing. As a result of this receiving focus processing, received data (sonic ray signals) are generated in which the focal points of the ultrasonic echoes are restricted.

The phase addition unit 38 supplies the received data to the detected wave processing unit 40.

The detected wave processing unit 40 carries out a correction for attenuation with distance on the received data generated by the phase addition unit 38, in accordance with the depth of the reflection position of the ultrasonic wave, and generates B mode image data, which is layered image information, for the organs within the inspection object, by carrying out envelope detected wave processing.

The DSC (digital scan converter) 48 converts the B mode image data generated by the detected wave processing unit 40 into image data in accordance with the normal television signal scanning format (raster conversion).

The image producing unit 44 carries out various required types of image processing such as gradation processing on the B mode image data input from the DSC 42, to produce B mode image data for inspection and display, then outputs the generated B mode image data for inspection or display to the display control unit 26 for display, or stores to the image memory 46 for storage.

The image memory 46 temporarily stores the B mode image data for inspection produced by the image producing unit 44. When necessary, the B mode image data for inspection stored in the image memory 46 is read out by the display control unit 26 for display on the display unit 28.

The display control unit 26 displays the ultrasound image on the display unit 28 based on the B mode image signals for inspection on which image processing was carried out by the image producing unit 44.

The display unit 28 includes, for example, a display device such as an LCD (Liquid Crystal Display), and displays ultrasound images under the control of the display control unit 26.

The control unit 30 controls each unit of the ultrasound inspection device 10 based on commands input by an operator from the operation unit 32.

Here, when necessary, the control unit 30 supplies to each of the units such as the transmitter 14, the receiver 16, the element data storage unit 20, the element data processing unit 22, the image generating unit 24, the display control unit 26, and the focal point setting unit 96, various types of information from the operator via the operation unit 32, in particular when information necessary for setting the transmission focal points by the focal point setting unit 96, and, information necessary for processing the element data by the element data processing unit 22 is input, the above various information is input from the operation unit 32.

The operator carries out input operations using the operation unit 32, which can be formed from a keyboard, a mouse, a trackball, a touch panel or the like.

Also, the operation unit 32 includes an input device for the operation of inputting various kinds of information by the operator as necessary, in particular information regarding the display region (inspection range), depth, transducer array 36, transmission focal point position, and the like that is used for setting the transmission focal point as described above; information regarding the velocity of sound in the regions of the inspection objects being inspected, the transmission aperture and receiving aperture of the transducer array 36, and the like that is used for processing element data; as well as information regarding element data processing such as the number of element data superimposed and the method of superimposition processing.

The storage unit 34 stores various types of information input from the operation unit 32, in particular information regarding the display unit as described above, the depth, the probe 12 (transducer array 36), the velocity of sound, the position of the transmission focal point, the transmission aperture and the receiving aperture, and the like, information regarding element data processing such as the number of element data superimposed and the superimposition processing method, information necessary for processing and operation of each unit controlled by the control unit 30, such as the transmitter 14, the receiver 16, the element data storage unit 20, the element data processing unit 22, the image generating unit 24, and the display control unit 26, as well as, stores operation programs and processing programs and the like for executing processing and operations in each unit, and can use a storage medium such as a hard disk, a flexible disk, an MO (Magneto-Optical disk), an MT (Magnetic Tape), a RAM (Random Access Memory), a CD-ROM (Compact Disc Read Only Memory), and a DVD-ROM (Digital Versatile Disk Read Only Memory).

Note that the element data processing unit 22, the phase addition unit 38, the detected wave processing unit 40, the DSC 42, the image producing unit 44, the focal point setting unit 96, a focal point resetting unit 98, and the display control unit 26 comprise a CPU (Central Processing Unit) and operation programs that cause the CPU to execute various processing, but they may also comprise digital circuits.

Here, the element data processing unit 22 is described in detail based on FIG. 3.

As shown in this drawing, the element data processing unit 22 includes a delay time calculation unit 48, a mode switching unit 49, and a superimposition processing unit 50.

The mode switching unit 49 switches the mode in accordance with the determination result of the calculation point positional determination unit 94 when the delay time calculation unit 48 calculates the delay time.

Specifically, the mode switching unit 49 switches the mode of the delay time calculation unit 48 in accordance with the determination result of the calculation point positional determination unit 94 so that the delay time is calculated in the first mode as described later for sampling points in which the distance to the focal point is greater than the predetermined threshold, and the delay time is calculated in the second mode as described later for sampling points in which the distance to the focal point is less than the predetermined threshold.

The delay time calculation unit 48 calculates the delay time of the element data received by each ultrasound element of the receiving aperture based on information regarding the plurality of ultrasound elements of the transducer array 36 of the probe 12, the velocity of sound of the region of the inspection object being inspected, the transmission aperture and the receiving aperture of the transducer array 36, and the like, input from the operation unit 32, or input from the operation unit 32 and the stored in the storage unit 34, and, information acquired in advance regarding the transmission focal point set by the focal point setting unit 96, and the geometric arrangement of the ultrasound elements (transmission elements) of the transmission aperture that form and transmit the ultrasonic beam, and the ultrasound elements (receiving elements) of the receiving aperture that receives the ultrasonic echoes of the ultrasonic beam from the inspection object.

The delay time calculation unit 48 includes the first mode (convergent wave mode) that obtains the delay time from the transmission path of the ultrasonic beam when the ultrasonic beam is modeled as convergent wave, and the second mode (planar wave mode) that obtains the delay time from the transmission path of the ultrasonic beam when the ultrasonic beam is modeled as a planar wave, and calculates the delay time after switching the mode for each sampling point by the mode switching unit 49.

The convergent wave mode and the planar wave mode are described in detail later.

For each sampling point, the superimposition processing unit 50 reads out two or more element data obtained by transmitting ultrasonic beams to different transmission lines stored in the element data storage unit 20, based on information regarding the element data processing such as the number of superimposed data and the method of superimposition processing, input from the operation unit 32 or input from the operation unit 32 and stored in the storage unit 34, and generates superimposition processed data in which two or more unprocessed element data are aligned in terms of receiving time, in other words their times are aligned, and, the absolute positions of the elements of the receiving probe are aligned, based on their respective delay times calculated by the delay time calculation unit 48, focusing on predetermined points (sampling points) of the line of interest where the superimposition is to be carried out.

Next, the element data processing carried out by the element data processing unit 22 is described in detail.

First, the relationship between the transmission beam from the transmission elements and the element data obtained from the receiving elements is described, when the ultrasonic beam (hereafter referred to as the transmission beam) from the ultrasound elements (hereafter referred to simply as transmission elements) that constitute the transmission aperture of the transducer array 36 of the ultrasound probe 12 is transmitted to the inspection object, and when the ultrasonic echoes generated by interaction with the inspection object are received as element data (unprocessed element data) by the ultrasound elements (hereafter simply referred to as receiving elements) that constitute the receiving aperture of the transducer array 36.

FIGS. 4A and 4C schematically show, as examples, the positions of each ultrasound element, ultrasonic beam, focal point, and the ultrasonic echoes in the case where transmission lines are set corresponding to each ultrasound element in the direction normal to the direction of an array of ultrasound elements, and a single focal point position is set on each transmission line.

As shown in FIGS. 4A and 4C, when ultrasonic echoes are received and element data is obtained using respectively the three ultrasound elements 52c to 52e and 52d to 52f as transmission elements, and seven ultrasound elements (hereafter simply referred to as elements) 52a to 52g and 52b to 52h as receiving elements respectively, when the transmission beam 56 that is transmitted to a inspection region that includes a reflection point 54 is ideally focused to the spacing of the elements or less, the transmission beam 56 is transmitted on the transmission line corresponding to the element 52d directly above the reflection point 54 within the inspection object using the elements 52c to 52e as transmission elements with the element 52d at the center of elements 52a to 52g as the central element, as shown in FIG. 4A, and when element data is obtained by receiving the ultrasonic echoes at the receiving elements 52a to 52g, a focal point 58 of the transmission beam 56 is on the straight line connecting the element 52d and the reflection point 54, and the transmission beam 56 is transmitted to the reflection point 54, so transmission echoes reflected from the reflection point 54 are generated. The ultrasonic echoes from the reflection point 54 pass through a receiving path 60 spreading at a predetermined angle and are received by the receiving elements 52a to 52g, so element data 62 as shown in FIG. 4B is obtained by the receiving elements 52a to 52g.

In contrast, when the center of the transmission elements is shifted in the direction of the elements (the right side in the drawing) by one element with respect to the reflection point 54, as shown in FIG. 4C, in other words, when the transmission beam 56 is transmitted on the transmission line corresponding to the element 52e with the elements 52d to 52f as transmission elements and the element 52e that is adjacent to the element 52d as the central element directly above the reflection point 54 and the ultrasonic echoes are received by the receiving elements 52b to 52h, the reflection point 54 is not in the transmission beam 56 transmission direction, in other words, is not on the straight line (on the transmission line) connecting the transmission element 52e and the focal point 58, so the transmission beam 56 is not transmitted to the reflection point 54. Therefore, there is no ultrasonic echo generated by reflection from the reflection point 54, and the receiving elements 52b to 52h do not receive ultrasonic echoes, so as shown in FIG. 4D, the element data is data with signal strength zero.

However, as shown in FIGS. 5A and 5C, the actual transmission beam 64 is wider than the spacing of the elements.

Here, as shown in FIG. 5A, when the transmission beam 64 is transmitted on the transmission line corresponding to the element 52d which is directly above the reflection point 54 with the elements 52c to 52e as transmission elements and the element 52d as the central element, the same as in FIG. 4A, and regardless of whether the transmission beam 56 is broad, the focal point 58 is on the straight line connecting the element 52d and the reflection point 54, the transmission beam 64 is reflected by the reflection point 54, and ultrasonic echoes are generated. As a result, the ultrasonic echoes from the reflection point 54 pass through the receiving path 60 that spreads at a predetermined angle and are received by the receiving elements 52a to 52g, the same as in FIG. 4A, and genuine element data 66 can be obtained by the receiving elements 52a to 52g, as shown in FIG. 5B.

On the other hand, as shown in FIG. 5C, when the center of the transmission elements is shifted in the direction of the elements (the right side in the drawing) by one element with respect to the reflection point 54, the same as in FIG. 4C, in other words, when the transmission beam 64 is transmitted on the transmission line corresponding to the element 52e with the elements 52d to 52f as transmission elements and the element 52e that is adjacent to the element 52d as the central element directly above the reflection point 54 and the ultrasonic echoes are received by the receiving elements 52b to 52h, because the transmission beam 64 is broad, even though the reflection point 54 is not in the transmission direction, in other words on the straight line connecting the transmission element 52e and the focal point 58, the transmission beam 64 is transmitted to the reflection point 54. Therefore, the ultrasonic echoes reflected by the reflection point 54 pass through the receiving path 60 that spreads at a predetermined angle and are received by the receiving elements 52b to 52h, so the element data 68 that has been affected by the reflection point as shown in FIG. 5D can be obtained by the receiving elements 52b to 52h.

Sonic ray signals are generated from element data 68 that is affected by reflection points other than those on the transmission line (hereafter also referred to as ghost element data), so when an ultrasound image is generated, an image of a reflection point that does not actually exist is reproduced on the image of the line corresponding to the element 52e to generate the so-called ghost, which causes the accuracy of the ultrasound image to be reduced.

Here, the sum of the transmission path of the transmission beam 64 from the transmission element 52e to the reflection point 54 via the focal point 58 and the receiving path of the ultrasonic echoes from the reflection point 54 to each receiving element 52b to 52h as shown in FIG. 5C (the propagation distance) is longer than the sum of the transmission path of the transmission beam 64 from the transmission element 52d to the reflection point 54 via the focal point 58 and the receiving path of the reflected ultrasonic echoes from the reflection point 54 to each receiving element 52a to 52g as shown in FIG. 5A (the propagation distance). Therefore, the ghost element data 68 shown in FIG. 5D is delayed with respect to the genuine element data 66 as shown in FIG. 5D.

In the delay time calculation unit 48 of the element data processing unit 22 according to the present invention, the time difference, in other words the delay time, is calculated between the element data obtained by transmitting and receiving an ultrasonic wave on the transmission line of interest from the sampling point on the transmission line of interest and the geometric arrangement of the central element corresponding to each transmission line (hereafter referred to as the element data of interest) and the element data obtained by transmitting and receiving an ultrasonic wave on a transmission line that is different from the transmission line of interest (hereafter referred to as element data not of interest). Therefore, information such as the shape of the ultrasound probe 12 (transducer array 36) (element spacing, linear, convex, and the like) the velocity of sound in the region of the inspection object being examined, the focal point position, the transmission aperture, the receiving aperture, and the like is necessary for calculating the delay time, so the delay time calculation unit 48 acquires information on the focal point position set by the focal point setting unit 96, information on the sampling points set by the calculation point setting unit 92, and information input by the operation unit 32 or stored in the storage unit 34, and calculates the delay time. The delay time is calculated from, for example, the geometric arrangement of the transmission element, the focal point of the ultrasonic beam, the sampling point, and the receiving element, and can be calculated from the difference in the propagation time calculated from the total length of the transmission path of the transmission beam from the transmission element passing through the focal point of the ultrasonic beam to the sampling point and the length of the receiving path of the reflected signal from the sampling point to the receiving element (propagation distance), and the propagation time calculated from the velocity of sound.

Here, as stated previously, in the present invention, there is the convergent wave mode in which the delay time calculation unit 48 considers the ultrasonic beam to be a convergent wave, in other words, the delay time is calculated by obtaining the total length of the transmission path of the transmission beam from the transmission element to the sampling point via the focal point and the length of receiving path of the reflected signal from the sampling point to the receiving element (propagation distance), with the focal point as a point (point sound source), and the planar wave mode in which the delay time is calculated by obtaining the total length of the transmission path and the receiving path with the ultrasonic beam considered to be a planar wave.

Figure 6A:
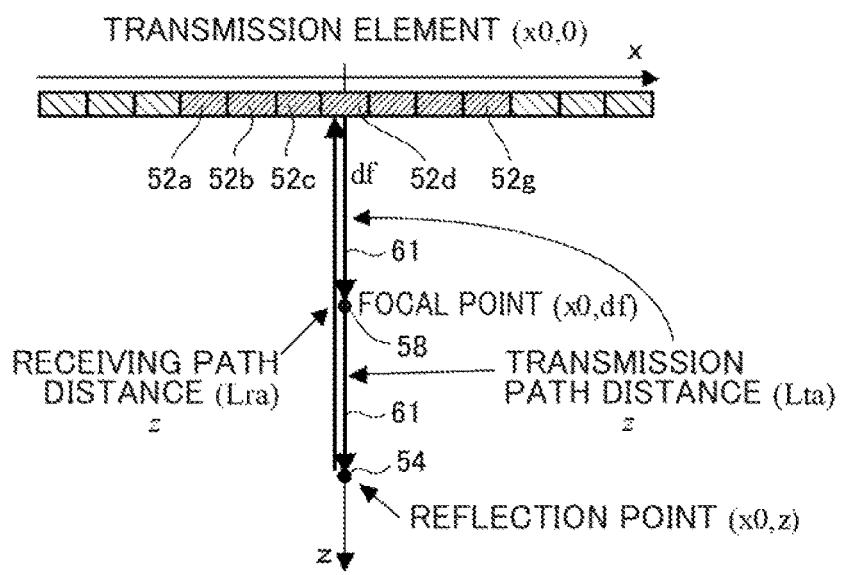
FIGS. 6A and 6B are explanatory views for describing the ultrasonic beam transmission path and receiving path distances for the genuine reflected ultrasonic echo and ghost reflected signal respectively.
Figure 6B:
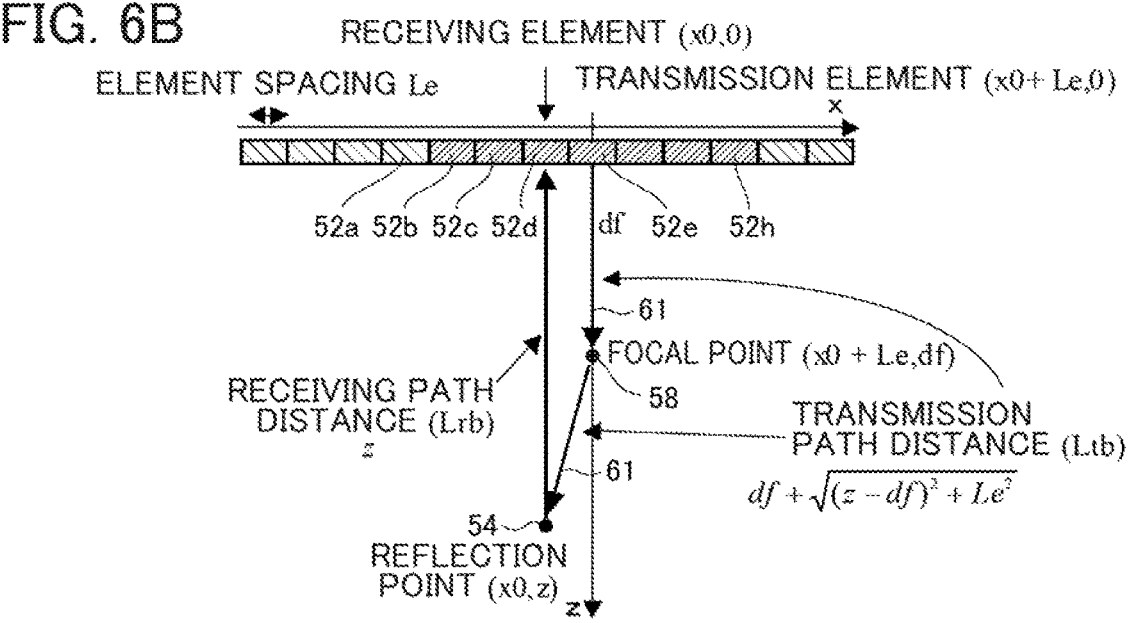

First, the convergent wave mode is described using FIGS. 6A and 6B.

In the convergent wave mode, the transmission beam first reaches (is focused onto) the focal point and then proceeds to the sampling point, and is modeled as reflected at the sampling point to calculate the transmission path.

Specifically, as shown in FIGS. 6A and 6B, the lengths of the transmission path of the ultrasonic beam and the receiving path of the ultrasonic echoes can be obtained for both the element data of interest and the element data of non-interest. In FIGS. 6A and 6B, for explanation it is assumed that the reflection point 54 is at the sampling point on the transmission line of interest.

As shown in FIG. 6A, in the case of the element data of interest, in other words, when the transmission line of interest (the transmission line of the sampling point) and the transmission line on which the ultrasonic beam was transmitted coincide, the central element of the transmission elements 52c to 52e and the central element of the receiving elements 52*a* to 52*g* coincide, and the focal point 58 and the reflection point 54 are disposed directly below. If the position of the element 52*d* directly above the reflection point 54 is defined in terms of 2-dimensional coordinates x and y as (x0, 0), the element spacing is Le, the coordinates of the position of the focal point 58 are (x0, df), and the coordinates of the position of the reflection point 54 are (x0, z), the coordinates of the position of the transmission element 52*d* are the same as the coordinates of the element 52*d* that is directly above the reflection point 54, namely (x0, 0), and the length of the transmission path 61 of the transmission beam from the transmission element 52*d* through the focal point 58 to the reflection point 54 (transmission path length) Lta, and the length of the receiving path 60 of the ultrasonic echo from the reflection point 54 to the receiving element 52*d* (receiving path length) Lra can be calculated from Lta=Lra=z.

Therefore, in the convergent wave mode, the propagation distance Lua of the ultrasonic wave in the case of the element data of interest is Lua=Lta+Lra=2 z.

On the other hand, as shown in FIG. 6B, in the case of the element data of non-interest, in other words, when an ultrasonic beam is transmitted on a transmission line adjacent to the transmission line of interest (on a transmission line different to that of the sampling point), the position of the central element of the transmission elements 52*d* to 52*f* is shifted with respect to the reflection point 54 (sampling point) laterally by one element (x-direction: the right direction in the drawing), and the focal point 58 is disposed directly below the element 52*e* which is the central element, but the reflection point 54 is disposed directly below the element 52*d*. The position of the receiving element 52*d* directly above the reflection point 54 in terms of the 2-dimensional xy coordinates are (x0, 0), the same as in FIG. 6A, and if the element spacing is Le and the coordinates of the reflection point are (x0, z), the coordinates of the position of the transmission element 52*e* are (x0+Le, 0), and the coordinates of the position of the focal point 58 are (x0+Le, df), so the length of the transmission path 61 of the transmission beam from the transmission element 52*e* through the focal point 58 to the reflection point 54 (transmission path length) Ltb can be calculated from Ltb=df+$\sqrt{\{(z-df)^2+Le^2\}}$, and the length of the receiving path 60*c* of the ultrasonic echo from the reflection point 54 to the receiving element 52*d* (receiving path length) Lrb can be calculated from Lrb=z.

Therefore, in the convergent wave mode, in the case of element data of non-interest, the propagation length of the element data of non-interest Lub is Lub=Ltb+Lrb=df+$\sqrt{\{(z-df)^2+Le^2\}}$+z.

In this way, the value obtained when the propagation distance Lua of the ultrasonic wave, which is the sum of the distance Lta of the transmission path 61 and the distance Lra of the receiving path 60 obtained for the geometrical arrangement shown in FIG. 6A, is divided by the velocity of sound is the propagation time between the ultrasound element and the sampling point when the ultrasonic wave for obtaining the element data of interest is transmitted and received. Also, the value obtained when the propagation distance Lub of the ultrasonic wave, which is the sum of the distance Ltb of the transmission path 61 and the distance Lrb of the receiving path 60 obtained for the geometrical arrangement shown in FIG. 6B, is divided by the velocity of sound is the propagation time between the ultrasound element and the sampling point when the ultrasonic wave for the transmission line adjacent to the transmission line for the element data of interest is transmitted and received.

The delay time is calculated by obtaining the difference between the delay time from the propagation time of the ultrasonic wave between the ultrasound element and the sampling point when obtaining the element data of interest, and the propagation time between the ultrasound element and the sampling point when obtaining the element data of non-interest.

In the geometric model of FIGS. 6A and 6B, the transmission path 61 is modeled as passing through the focal point 58, but the present invention is not limited to this, for example the path may go directly to the reflection point 54 without passing through the focal point 58.

Figure 7:
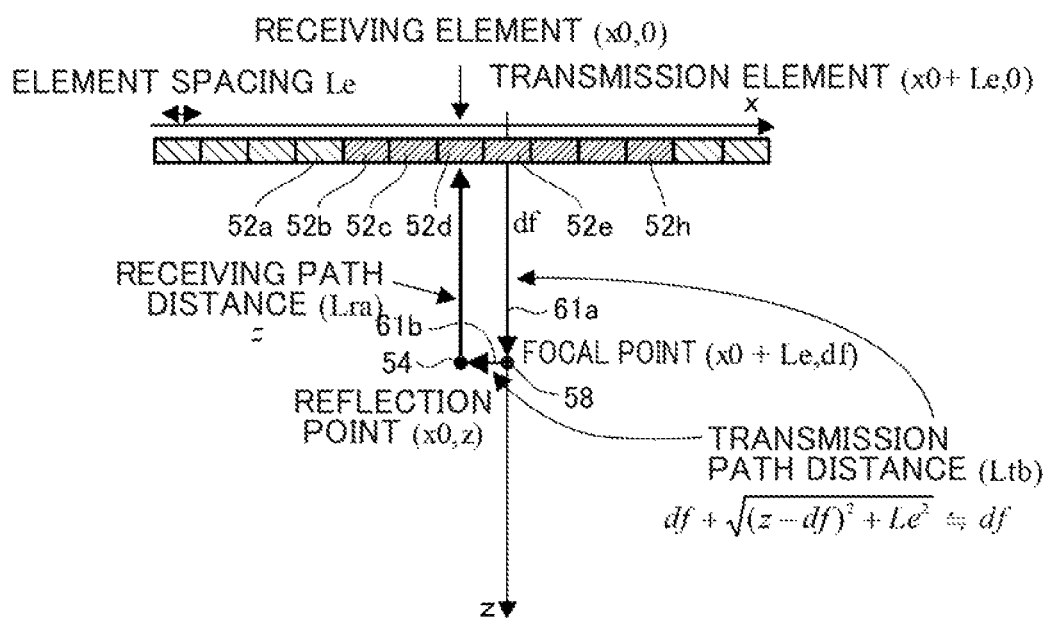
FIG. 7 is an explanatory view describing the planar wave mode.

Next, the planar wave mode is explained using FIG. 7.

In the planar wave mode, the transmission path is calculated by modeling the transmission beam as proceeding to the sampling point as a planar wave, without converging onto the focal point, and being reflected at the sampling point.

In the planar wave mode, it is possible to obtain the lengths of the transmission path of the transmission beam and the receiving path of the ultrasonic echoes for the element data of non-interest as shown in FIG. 7. The method of obtaining the transmission path and the receiving path in the case of the element data of interest is the same as that for the convergent wave mode, so its description is omitted here. Also, in FIG. 7, for explanation it is assumed that the reflection point 54 is at the sampling point.

As shown in FIG. 7, in the case of the element of non-interest, the position of the central element of the transmission elements 52*d* to 52*f* is shifted with respect to the reflection point 54 (sampling point) laterally by one element (x-direction: the right direction in the drawing), and the focal point 58 is disposed directly below the element 52*e* which is the central element, but the reflection point 54 is disposed directly below the element 52*d*, the same as in FIG. 6B. The position of the receiving element 52*d* directly above the reflection point 54 in terms of the 2-dimensional xy coordinates is (x0, 0), the same as in FIG. 6B, and if the element spacing is Le and the coordinates of the reflection point 54 are (x0, z), the coordinates of the position of the transmission element 52*e* are (x0+Le, 0), and the coordinates of the position of the focal point 58 are (x0+Le, df).

Here, in the case of the planar wave mode, the transmission beam transmitted from the plurality of transmission elements 52*d* to 52*f* can be considered to arrive at the reflection point 54 as a planar wave. In other words, the path from the focal point 58 to the reflection point 54 can be considered to be the path projected onto the z axis. Therefore in the case of a linear probe as shown in FIG. 7, the length Ltb of the transmission path is equal to the depth z of the reflection point 54.

Also, the length of the receiving path 60 of the ultrasonic echo from the reflection point 54 to the receiving element 52*d* (receiving path length) Lrb can be calculated from Lrb=z.

Therefore, in the planar wave mode, in the case of element data of non-interest, the propagation length of the ultrasonic wave for the element data of non-interest Lub is Lub=Ltb+Lrb=2 z.

In contrast, for a sampling point near the focal point, in the convergent wave mode, the length of the transmission path 61 of the transmission beam from the transmission element 52*e* through the focal point 58 to the reflection point 54 (transmission path length) Ltb is obtained from Ltb=df+$\sqrt{\{(z-df)^2+Le^2\}}$, but if the sampling point is near the focal point, z≈df, so Ltb=df+$\sqrt{\{Le^2\}}$=df+Le≈z+Le. In other words, it is longer than the length of the transmission path 61 obtained in the planar wave mode.

As stated above, in the convergent wave mode, the length of the transmission path is calculated considering the ultrasonic beam to be a convergent wave and the focal point to be a point, but the focal point of an actual ultrasonic beam is not converged sufficiently to be considered to be a point, and it has a finite width. Therefore, for a sampling point near the focal point, when the length of the transmission path is obtained in the convergent wave mode, it is longer than the length of the actual transmission path, and when the delay time is calculated from the calculated transmission path length, the difference from the actual delay time increases, and the accuracy of the superimposition of the element data is reduced.

Therefore, for a sampling point near the focal point, by calculating the delay time by obtaining the length of the transmission path in the planar wave mode, it is possible to prevent a reduction in the accuracy of superimposition of the unprocessed element data.

In the convergent wave mode, the method of calculating the delay time in the case of transmission and receiving an ultrasonic wave with a certain element as the central element is to take the delay time for an element 52 located directly below the sampling point as a representative value, and to use this representative value as the delay time for all elements in transmitting and receiving.

However, the present invention is not limited to this, for example the position in the x direction may be the sampling point such as the element 52c or the element 52b, in other words, the receiving path length Lrb for an element that is different from the element 52d directly below may be calculated from the element 52d directly below in accordance with the number of elements n, as $Lrb=\sqrt{\{(n \times Le)^2 + z^2\}}$.

Also, the geometric models in FIGS. 6A, 6B, and 7 are linear probes, but this is not a limitation, and in other types of probe also it is possible to carry out the same geometrical calculation for both the convergent wave mode and the planar wave mode from the shape of the probe. For example, in the case of a convex probe, the same type of calculation can be carried out by setting the geometric model from the radius of the probe and the angle of the element spacing.

Also, in the case of a beam steering transmission, using a geometric model (not shown on the drawings) taking into interest information such as the transmission angle, it is possible to calculate the delay time for the element data of interest and the nearby element data of non-interest, from the positional relationship between the transmission element and the sampling point.

Figure 6C:
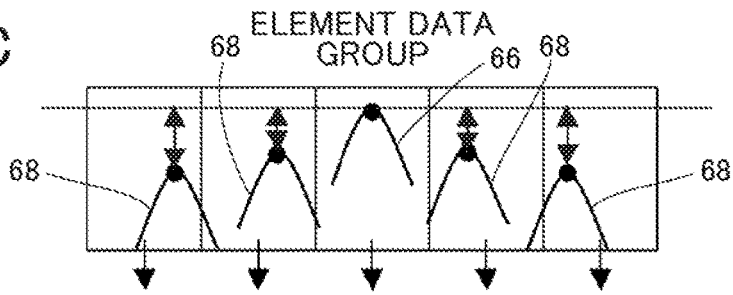
FIGS. 6C and 6D are explanatory views showing the element data obtained for the plurality of elements and their delay times respectively.
Figure 6D:
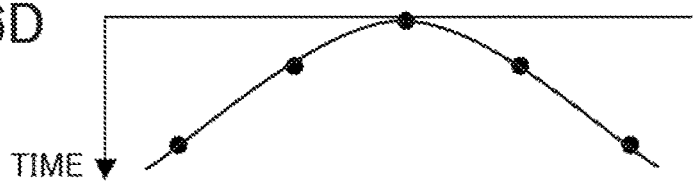

Next, in the convergent wave mode, the calculated delay time is described using FIGS. 6C and 6D.

FIG. 6C shows the center genuine element data 66 which is the element data in the case where the reflection point is on the transmission line, and ghost element data 68 on both sides thereof generated by ghosts as a result of the effect of the reflection point, and FIG. 6D shows an example of the delay times of the ghost element data 68 which is the element data of non-interest, when the element data of interest is the genuine element data 66 in the center, obtained from the geometric calculation. When the genuine element data 66 is the element data of interest, the ghost element data 68 is displayed as having the time symmetrically delayed.

In this way, the delay time calculated by the delay time calculation unit 48 of the element data processing unit 22 can be used in the delay correction of the phase addition unit 38.

Also, in the planar wave mode of the linear probe shown in FIG. 7, the propagation distance of the ultrasonic wave in the case of the element data of non-interest is the same as the propagation distance of the ultrasonic wave for the element data of interest, so the delay time is zero.

Next, in the superimposition processing unit 50 of the element data processing unit 22 of the present invention, for sampling points judged by the calculation point positional determination unit 94 to be outside a predetermined range of distance from the transmission focal point, using the delay time calculated in this way by the delay time calculation unit 48, superimposition processing is carried out on the element data of interest of the transmission line of interest, and the element data of non-interest which is the element data for the nearby transmission lines.

The convergent wave mode and the planar wave mode differ only in the method of calculating the delay time, and their superimposition processing is the same, so in the following description, the superimposition processing is described using the delay time calculated in the convergent wave mode.

In the superimposition processing of the superimposition processing unit 50, information regarding the number of element data to be superimposed and the superimposition processing method when superimposing is necessary, but this may be input in advance by the operation unit 32, or may be stored in the storage unit 34.

FIGS. 8A to 8H show a specific example of superimposition processing carried out by the superimposition processing unit 50 in a case where the number of element data is five and the number of superimposed element data is three.

Figure 8:
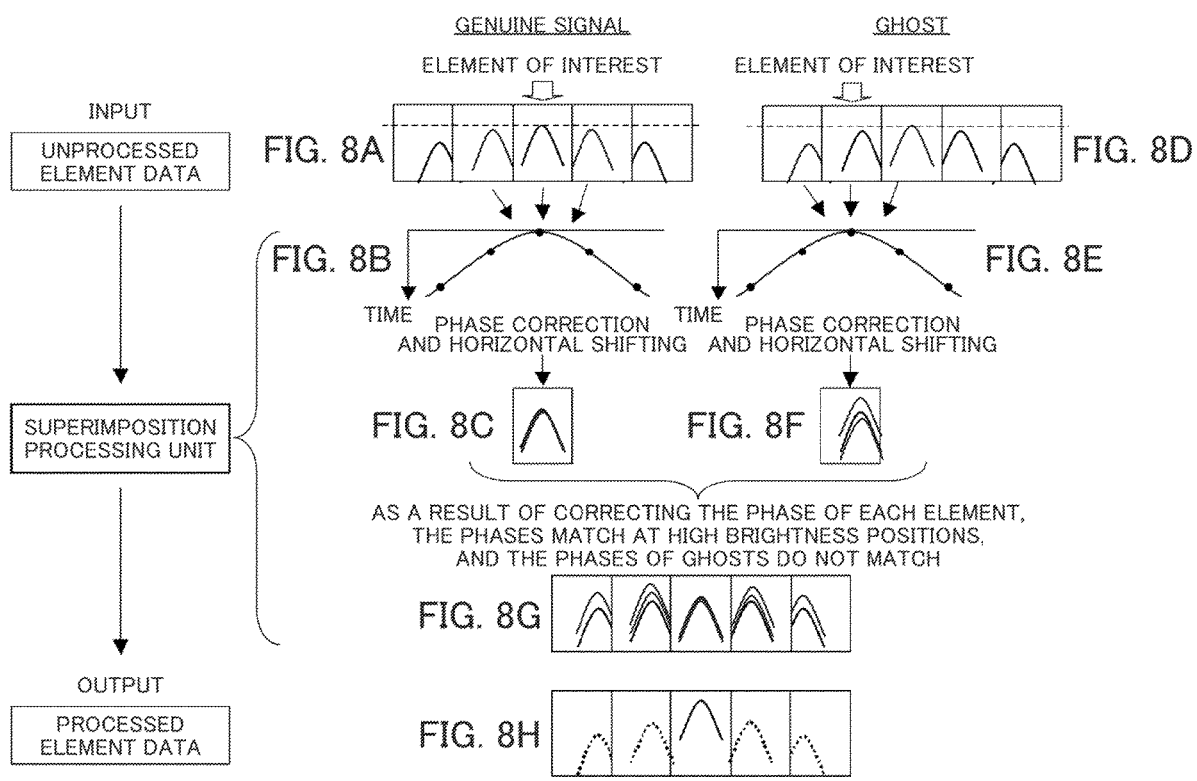
FIGS. 8A, 8B, and 8C, and FIGS. 8D, 8E, and 8F are explanatory views showing the element data obtained by the plurality of elements, their delay times, and the status of superposition of the element data for the genuine signal and the ghosts respectively.
FIGS. 8G and 8H are explanatory views showing the status of superposition of the element data corresponding to the plurality of elements and their results respectively.

FIG. 8A shows the five element data arranged horizontally for five adjacent elements, obtained by transmitting and receiving an ultrasonic wave on the transmission line for the central element, and for each element data, the reflected signal received after an ultrasonic beam is transmitted is represented. The horizontal axis for each element data represents the receiving element, and on each element data the central element when transmitting the ultrasonic beam is represented in the center. The vertical axis represents the time received.

Of the five element data, in the element data in the center, the central element of the element data (central element of receiving elements), in other words, the central element (transmission element) during transmission, is directly above the reflection point, and receives the reflection signal (ultrasonic echo) from the reflection point. In other words, this reflection signal is the genuine signal, and the central element data is the genuine element data.

Apart from the central element data, in the case of the two element data on both sides, during transmission there is no reflection point directly below the central element, but due to the spread of the transmitted ultrasonic beam the ultrasonic beam strikes the reflection point that is directly below the transmission element of the central element data, and the reflected signal produced, in other words the ghost, is imprinted. In the case of the ghost images, the further from the genuine signal, the longer the propagation time of the ultrasonic wave to the reflection point, so the time received is delayed compared with the genuine element data. Also, the position of the receiving element that first receives the reflection signal from the reflection point is the element directly above the reflection point, but the central element during transmission of the ultrasonic beam is in the center of the horizontal axis of the element data, so each element data is shifted by one element at a time from the central element, in other words, the transmission line is shifted by one line at a time, so in each element data the absolute position of the elements is shifted by one element each. In other words, in the central element data, the receiving element that first receives the reflection signal from the reflection point is the central element, but in the two adjacent element data the elements are shifted by one element each from the central element data, the right side element data is shifted by one element to the left, and the left side element data is shifted by one element to the right. In addition, the element data at both ends are shifted by two elements each from the central element data, and the right end element data is shifted by two elements to the left, and the left end element data is shifted by two elements to the right. In this way, not only is the receiving time of the ghosts delayed relative to the genuine signal, but also a deviation in the direction of the receiving element is also produced.

FIG. 8B shows an example of the delay time of the receiving time for the element data for the five elements shown in FIG. 8A with the central element data as the element data of interest, in other words, for a specific sampling point on the transmission line corresponding to the central element.

In the superimposition processing unit 50, using the delay time shown in FIG. 8B, in the case that the central element data is the element data of interest, with the element data of interest in the center, delay time correction is carried out on the number of element data to be superimposed, in the case shown on the drawing three element data, and by shifting element data in the horizontal direction by the amount of deviation of each central element from the central element (element of interest) corresponding to the transmission line of the element data of interest, or by just one element in the case shown on the drawing, the phase of each is aligned to superimpose the unprocessed element data for the three transmission lines, to obtain a single superimposed processed element data corresponding to the specific sampling point of the transmission line of interest. By carrying out this superimposition processing for a specific sampling point, it is possible to obtain element data as if the focal point was focused on the sampling point.

FIG. 8C shows the superimposed processed element data for a sampling point with a reflection point on the same line, obtained in this way.

The element data of the element of interest shown in FIG. 8A is element data from a genuine signal, so when delay time correction and horizontal shifting is carried out on the unprocessed element data of the adjacent elements on both sides of the element of interest to align their phases, the phases of the unprocessed element data of the adjacent elements and the unprocessed element data of the element of interest match so they are superimposed in a position with high brightness, as shown in FIG. 8C. Thus, if for example these element data are added, the element data will exhibit a large value (high brightness value), and if for example they are averaged to obtain the average value, an emphasized value (high brightness value) will be exhibited.

In contrast, FIG. 8D shows an example of a case with the same element data group as FIG. 8A, but where the element data on the left of the central element data, in other words ghost element data, is taken to be the element data of interest, in other words the processing is carried out for a sampling point on the transmission line adjacent to and to the left of the center.

FIG. 8E shows an example of the delay time of the receiving time in the case where the element to the left of and adjacent to the center is the element of interest. FIGS. 8A and 8D show the same element data group, so in the delay times shown in FIG. 8E only the element of interest is different, and is the same as in FIG. 8B.

In the superimposition processing unit 50, using the delay time shown in FIG. 8E, with the element of interest in the center, delay time correction is carried out on the number of element data to be superimposed, in the case shown on the drawing three element data, and by shifting element data in the horizontal direction by the amount of deviation between the element of interest and each central element, or by just one element in the case shown on the drawing, the unprocessed element data is superimposed for the three transmission lines, to obtain a single superimposed processed element data corresponding to the specific sampling point of the transmission line of interest. By carrying out this superimposition processing for a specific sampling point, it is possible to obtain element data as if the focal point was focused on the sampling point.

FIG. 8F shows the superimposed processed element data for the sampling point with a reflection point on the adjacent line, obtained in this way.

Because the element data of the element of interest shown in FIG. 8D is ghost element data, even when the delay time correction and the horizontal shifting is carried out on the unprocessed element data on both sides of the element of interest to align their phases, the phases of each of the unprocessed element data of the adjacent elements and the unprocessed element data of interest are not aligned, so they cannot be superimposed as shown in FIG. 8F. Therefore, even if these three element data are added, for example, their phases do not align, so signals with their phases reversed and the like are canceled out, and the value of their sum does not increase, and if for example they are averaged to obtain an average value a small value will be displayed.

For the other element data also, FIG. 8G shows the state of superimposition of the element data for three adjacent transmission lines for the five element data shown in the drawing as a result of carrying out delay time correction and horizontal shifting in the same way as for the element data of interest, and FIG. 8H shows the results of, for example, addition processing or averaging processing as the superimposition processing.

As shown in FIG. 8H, when in the case of the transmission line of interest the coordinates of the central element of the transmission element shown in FIG. 8A and the reflection point coincide (when there is a reflection point on the transmission line), the element data for the genuine signal is obtained as a superimposed processed element data having a high brightness value, but for the two elements on both sides or a total of four elements, when the ghost element data for element data with phases that do not align are added or averaged, they cancel each other out so the ghost superimposed processed element data have values that are small compared with the element data for the genuine signal which is superimposed processed element data having high brightness values, so the effect of the ghost element data on the element data of the genuine signal is reduced, or, can be made so small that its effect can be ignored.

Note that the method of superimposition processing in the superimposition processing unit 50 need not be simply summation, but taking an average value or median value may be carried out, or summation may be carried out after multiplication by a coefficient. Note that it is considered that taking an average value or a median value is equivalent to applying an averaging filter or a median filter to the element data level, but an inverse filter or the like as carried out in normal image processing may also be applied instead of an averaging filter or a median filter. Alternatively, each of the element data to be superimposed may be compared with each other, and if similar the maximum value may be taken, if not similar an average value may be taken, and if there is bias in the distribution a median value may be taken, and the like, but this is not a limitation, and the superimposition processing may be changed based on a characteristic quantity of each of the element data to be superimposed.

Also, it is desirable that the number of element data to be superimposed be adjusted to suit the spread of the beam width of the ultrasonic beam. Therefore, if the beam width changes with depth, the number of element data to be superimposed may also be varied with depth. Also, the beam width depends on the number of the transmission apertures, so the number of element data to be superimposed may also be varied with the number of the transmission apertures. Alternatively, the number of element data to be superimposed may also be varied based on a characteristic quantity such as the brightness value of the image, or the number of element data to be superimposed may be selected by changing a plurality of patterns and selecting the ideal number of element data to be superimposed from the images produced.

As a result of the superimposition, as stated above, the phases of the signals are aligned for the element data for the genuine signal, but for the ghosts the phases of the signals do not align, so as a result of superimposition processing such as summation, the signals with various phases cancel each other out, so the signal is weakened. As a result, the genuine signal has an effective value, and for example remains as high brightness element data, but the ghost signals have reduced values, so it is possible to obtain them as, for example, low brightness element data.

As stated above, if a plurality of transmission beams is generated while changing the transmission position in order to produce data for one line in order to obtain high-quality images, the number of transmissions is increased so the frame rate is reduced, which has the problem that the real-time properties become poorer.

Also, when correcting the delay times of a plurality of reception signals and synthesizing them, when calculating the delay time, if the focal point is considered to be a point (point sound source) when calculating the transmission path, in reality the focal point of the transmitted ultrasonic beam is not focused to the extent that it can be considered to be a point, but it is spread with a finite width, so close to the focal point, the error relative to the actual transmission path of the ultrasonic beam becomes large, so the error between the actual delay time and the calculated delay time becomes large. If the reception signal is synthesized using this delay time, the data accuracy is reduced, which has the problem that the image SN ratio and the resolution are reduced.

In contrast, the present invention is switched between the first mode that superimposes the element data assuming the ultrasonic beam to be a convergent beam, and the second mode that superimposes the element data assuming the ultrasonic beam to be a planar wave, depending on whether the distance between the sampling point and the focal point is within the predetermined range or not, and the first element data is superimposed to generate the second element data. Specifically, if it is judged that the sampling point is outside the predetermined range of distance from the focal point, in other words, if it is far from the focal point, the deviation between the receiving times, in other words the delay time, is calculated between unprocessed element data to be superimposed (first element data) from the transmission distance of the ultrasonic wave calculated by considering the ultrasonic beam to be a convergent beam, and based on this delay time and information on the geometric arrangement of the elements, the plurality of unprocessed element data is synthesized, to generate new processed element data (second element data) corresponding to the sampling point. On the other hand, if it is judged that the sampling point is within the predetermined range of distance from the focal point, in other words, if it is near to the focal point, the delay time is calculated from the transmission distance of the ultrasonic wave calculated by considering the ultrasonic beam to be a planar wave, and based on this delay time and information on the geometric arrangement of the elements, the plurality of unprocessed element data is synthesized, to generate new processed element data corresponding to the sampling point.

In this way, for sampling points far from the focal point, it is possible to reduce the effect of ghosts generated by the spread of the ultrasonic beam even for positions distant from the focal point, by carrying out the superimposition of a plurality of first element data, and it is possible to obtain element data (second element data) for each sampling point as when a focal point is formed. Therefore, it is sufficient to carry out transmission and reception once for one transmission line, so it is possible to obtain high accuracy element data without increasing the number of transmissions and receptions, without reducing the frame rate, thereby maintaining the real time properties, and improving the SN ratio and resolution of the image.

In addition, for sampling points near the focal point, calculation of the delay time for superimposition is carried out with appropriate modeling of the ultrasonic beam near the focal point, so it is possible to generate second element data without reducing the accuracy of the superimposition near the focal point.

As a result of the above, the ultrasound inspection device according to the present invention can improve the SN ratio and resolution of the whole image, and, it is possible to obtain sharp ultrasound images having high resolution and the ideal spatial resolution, with a frame rate that is no different from the conventional technology.

Also, it is possible to obtain high quality element data, so when obtaining the ideal velocity for each region within the regions of the inspection object using the element data, it is possible to obtain the high accuracy ideal velocity.

The following is a description of the operation and action of the ultrasound inspection device and the ultrasound image data generation method according to the present invention.

Figure 9:
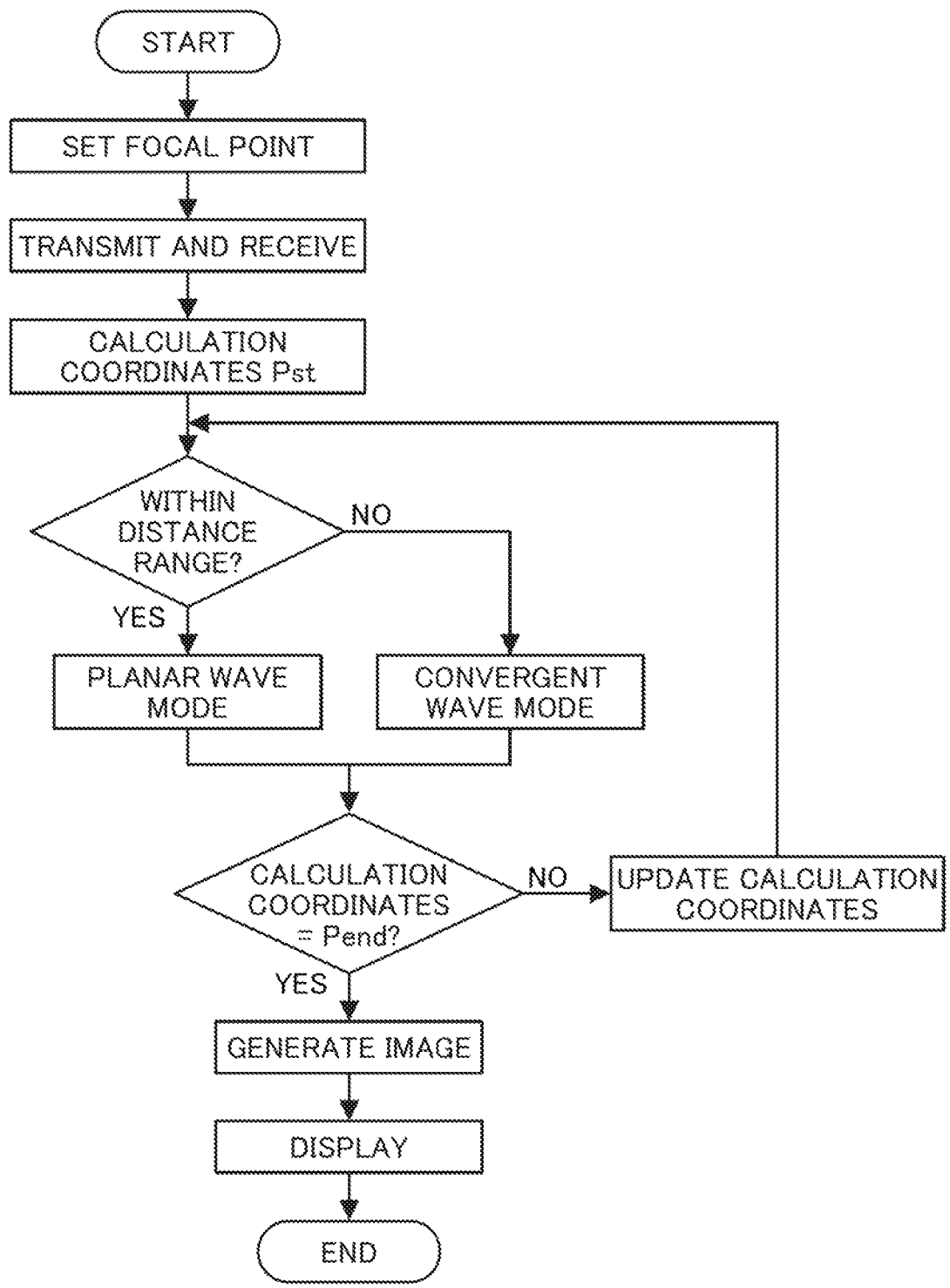
FIG. 9 is a flowchart describing the operation of the ultrasound inspection device shown in FIG. 1.

FIG. 9 is a flowchart describing the operation of the ultrasound inspection device shown in FIG. 1.

First, the focal point setting unit 96 sets the position of the focal point in accordance with information input from the operation unit 32, and information regarding the set focal point position is supplied to the transmitter 14 and calculation point positional determination unit 94.

Also, the calculation point setting unit 92 sets the data calculation points (sampling points) in accordance with information input from the operation unit 32, and supplies it to the calculation point positional determination unit 94.

The calculation point positional determination unit 94 determines whether or not each sampling point is within a predetermined range of distance from the focal point, based on the supplied information on the sampling points and the focal point position, and supplies the determination result to the element data processing unit 22.

The operator brings the ultrasound probe 12 into contact with the surface of the inspection object, and when the measurement is started, an ultrasonic beam is transmitted from the transducer array 36 in accordance with drive signals supplied from the transmitter 14, the ultrasonic echoes are received from the inspection object by the transducer array 36, and an analog element signal is output as the reception signal. At this time, the transmitter 14 drives the transducer array 36 to transmit the ultrasonic beam forming the focal point at the focal point position supplied from the focal point setting unit 96.

The receiver 16 outputs the analog element signal output by each element as single analog element data, and supplies it to the A/D converter 18. The A/D converter 18 converts the analog element data to digital element data, and supplies it to the element data storage unit 20 to be stored.

The element data processing unit 22 calculates the delay time (for example, the same as either FIG. 8B or FIG. 8E) between the unprocessed element data for the transmission line of interest and the unprocessed element data for the nearby transmission lines in the delay time calculation unit 48 (FIG. 3) for each sampling point, from the geometrical arrangement of the transmission elements, the focal point, the reflection point, and the receiving elements, the velocity of sound in the region of the inspection object to be inspected that is input and set in advance (for example, calculation using the geometric model shown in FIGS. 6A and 6B).

Next, the element data processing unit 22 carries out processing on each sampling point sequentially (from the calculation coordinate Pst to calculation coordinate Pend) in accordance with the determination result of the calculation point positional determination unit 94. If the distance between the sampling point and the focal point is outside the predetermined range, the delay time is calculated in convergent wave mode, a plurality of unprocessed element data is read out from the element data storage unit 20 including the unprocessed element data of the transmission line corresponding to the sampling point, the element data to be processed is taken to be the element data of interest, and in the superimposition processing unit 50 (FIG. 3) the superimposed processed element data is obtained by aligning the phases of the element data of interest and the unprocessed element data for the nearby transmission lines (element data of non-interest) using the delay times calculated by the delay time calculation unit 48. Also, if the distance between the sampling point and the focal point is within the predetermined range, the delay time is calculated in planar wave mode, a plurality of unprocessed element data is read out from the element data storage unit 20 including the unprocessed element data of the transmission line corresponding to the sampling point, the element data to be processed is taken to be the element data of interest, and in the superimposition processing unit 50 (FIG. 3) the superimposed processed element data is obtained by aligning the phases of the element data of interest and the unprocessed element data for the nearby transmission lines (element data of non-interest) using the delay times calculated by the delay time calculation unit 48.

In this way, processed element data is obtained in which the genuine signal is emphasized, and the ghost signals are reduced.

The element data obtained in this way is supplied to the phase addition unit 38 of the image generating unit 24.

The phase addition unit 38 of the image generating unit 24 carries out receiving focus processing on the processed element data to generate received data (sonic ray signal), and supplies it to the detected wave processing unit 40. The detected wave processing unit 40 processes the sonic ray signals to generate a B mode image signal. The B mode image signal is converted into raster by the DSC 42, and the image producing unit 44 carries out image processing to generate the ultrasound image. The generated ultrasound image is stored in the image memory 46, and the ultrasound image is displayed on the display unit 28 by the display control unit 26.

In this way, the ultrasound inspection device 10 according to the present invention is switched between the first mode that superimposes the element data assuming the ultrasonic beam to be a convergent beam, and the second mode that superimposes the element data assuming the ultrasonic beam to be a planar wave, depending on whether the distance between the sampling point and the focal point is within the predetermined range or not, and the first element data is superimposed to generate the second element data.

In this way, for sampling points far from the focal point, it is possible to reduce the effect of ghosts generated by the spread of the ultrasonic beam even for positions distant from the focal point, by carrying out the superimposition of a plurality of first element data, and it is possible to obtain element data (second element data) for each sampling point as when a focal point is formed. Therefore, it is sufficient to carry out transmission and receiving once for one transmission line, so it is possible to obtain high accuracy element data without increasing the number of transmissions and receptions, without reducing the frame rate, thereby maintaining the real time properties, and improving the SN ratio and resolution of the image.

In addition, for sampling points near the focal point, calculation of the delay time for superimposition is carried out with appropriate modeling of the ultrasonic beam near the focal point, so it is possible to generate second element data without reducing the accuracy of the superimposition near the focal point.

As a result of the above, the ultrasound inspection device according to the present invention can improve the SN ratio and resolution of the whole image, and, it is possible to obtain sharp ultrasound images having high resolution and the ideal spatial resolution, with a frame rate that is no different from the conventional technology.

Also, it is possible to obtain high quality element data, so when obtaining the ideal velocity for each region within the regions of the inspection object using the element data, it is possible to obtain the high accuracy ideal velocity.

In the embodiment as described above, the element data superimposed with the element data of interest was element data for transmission lines adjacent to the transmission line of the element data of interest, but the present invention is not limited to this, provided it is a transmission line that is different from the transmission line of the element data of interest. When superimposing the element data, preferably the region of the transmission beam transmitted when obtaining each element data overlaps with the region of the transmission beam transmitted when obtaining the element data of interest. Therefore, the element data that is to be superimposed with the element data of interest is preferably the element data of an adjacent line, or a nearby transmission line.

Also, the element data that is to be superimposed with the element data of interest is preferably element data from transmission lines that are symmetrical about the transmission line of the element data of interest as center, in other words, element data obtained by transmitting and receiving an ultrasonic wave with elements symmetrical about the element of interest as the central elements.

Also, in the embodiment as described above, it is configured that when the sampling point is far from the focal point, the delay time is calculated in convergent wave mode, and when near the focal point the delay time is calculated in planar wave mode, but the present invention is not limited to this, and the delay time may be calculated in convergent wave mode when the sampling point is far from the focal point, and the delay time may be calculated in planar wave mode when close to the focal point, and in intermediate cases the delay time may be calculated by a combination of the convergent wave mode and the planar wave mode. In other words, when the distance between the sampling point and the focal point is equal to or exceeds a predetermined first threshold, the delay time is calculated in convergent wave mode, when equal to or less than a second threshold that is smaller than the first threshold, the delay time is calculated in planar wave mode, and when between the first threshold and the second threshold, the delay time may be calculated from an average weighted in accordance with the distance to the focal point of the delay time calculated in the convergent wave mode and the delay time calculated in the planar wave mode.

Specifically, for example in the delay time calculation unit 48, when calculating the delay time, the equation for obtaining the length of the transmission path Ltb may be $Ltb = df + \sqrt{\{(z-df)^2 + \alpha(Le)^2\}}$, and $\alpha$ is varied in accordance with the distance from the focal point, and at the position of the focal point $\alpha=0$, and at a position equal to or greater than a predetermined distance $\alpha=1$. In this way, at the position of the focal point, the length of the transmission path (the delay time) is calculated in the planar wave mode, and at positions equal to or greater than a predetermined distance from the focal point, the length of the transmission path is calculated in the convergent wave mode, and at intermediate positions, the length of the transmission path is calculated from the weighted average of the planar wave mode and the convergent wave mode.

In this way, it is possible to prevent the production of a discontinuous point at the position of switching between the convergent wave mode and the planar wave mode, and it is possible to obtain a smoother image.

Also, in the embodiment as described above, the processing by the element data processing unit 22 (delay time calculation unit 48) is configured to be switched between the convergent wave mode and the planar wave mode in accordance with the distance between the sampling point and the focal point, but the present invention is not limited to this, but at all sampling points a first image may be generated using the processed element data processed in convergent wave mode, and, at all sampling points a second image may be generated using the processed element data processed in planar wave mode, and a new image may be generated in accordance with the distance from the focal point produced from the first image at positions far from the point, and produced from the second image at positions close to the focal point.

Also, in the embodiment as described above, the ultrasonic beam is configured to be transmitted in a direction normal to the direction of the array of ultrasound elements, but this is not a limitation, and the ultrasonic beam may be configured to be transmitted in a direction that is inclined (beam steering transmission) with respect to the direction of the array of ultrasound elements. Also, in the embodiment as described above, one set of transmission elements (transmission aperture) and one transmission of the ultrasonic beam are configured to correspond one-to-one, but this is not a limitation, and a plurality of ultrasonic beams may be configured to be transmitted in different directions using the same set of transmission elements.

Also, in the embodiment as described above, the center of the transmission elements is the same element as the center of the receiving elements but they may also be different. Also, in the drawings, the number of the transmission aperture and the number of the receiving aperture were different, but the number of the apertures may be the same, and the receiving elements may be the same elements as the transmission elements.

Also, the ultrasound inspection device according to the present embodiment is controlled by an ultrasound image data generating program stored in the memory of a control unit that is not shown on the drawings. Namely, the ultrasound image data generating program is read out from the memory by the control unit, and the functions of setting the focal point and sampling point, transmission of the ultrasonic beam to the inspection object in accordance with the set focal point, receiving the ultrasonic echoes reflected from the inspection object, selection of the mode in accordance with the distance from the focal point for each sampling point, synthesis of the obtained first element data by receiving the ultrasonic echoes, and generation of the second element data are executed in accordance with the ultrasound image data generating program.

That is, this memory in which the program is stored is the computer-readable recording medium in which is stored a signal processing program of the ultrasound inspection device according to the present invention.

The ultrasound image data generating program is not limited to being stored in a memory belonging to the control unit, but the ultrasound image data generating program may, for example, be recorded on a memory medium configured to be inserted into and removed from the ultrasound image processing device such as a CD-ROM (removable medium), and may be configured to be read into the device via an interface corresponding to the removable medium. That is, the recording medium according to the present invention may be a removable medium.

The ultrasound inspection device, the ultrasound image data generation method, and the computer-readable recording medium in which is stored the program according to the present invention have been described in detail above, but the present invention is not limited to the examples as described above, and various improvements or modifications may be made without departing from the essence of the present invention.

What is claimed is:

1. An ultrasound inspection device for inspecting an object to be inspected using an ultrasonic beam, comprising:
   a focal point setting unit for setting a plurality of transmission focal points within the object to be inspected;
   a probe including a plurality of elements, the plurality of elements generating each of the components of the ultrasonic beam and receiving ultrasonic echoes reflected by the object to be inspected and outputting received analog element signals;
   a transmitter for causing the probe to generate the ultrasonic beam towards each of the transmission focal points set by the focal point setting unit, using the plurality of elements;
   a receiver for receiving the analog element signals received by the plurality of elements corresponding to transmission of each of the ultrasonic beams towards each of the transmission focal points, and performing predetermined processing;
   an A/D converter for carrying out A/D conversion on analog element signals processed by the receiver, to produce first element data being digital element signals;

a calculation point setting unit for setting at least one data calculation point within the object to be inspected;

a calculation point positional determination unit for determining for each of the data calculation points set by the calculation point setting unit whether or not the distance to the transmission focal point is equal to or less than a predetermined threshold; and an element data processing unit which acquires first element data of interest and at least one of first element data in which a central element at the time of ultrasonic beam transmission is different from that of the first element data of interest, shifts the first element data different in central element by an amount of deviation with respect to the central element of the first element data of interest, performs delay time correction on the first element data different in central element, superimposes the first element data of interest and the first element data different in central element, and generates second element data corresponding to the data calculation points; wherein the focal point setting unit, the calculation point setting unit, the calculation point positional determination unit, and the element data processing unit are configured by a central processing unit (CPU) and an operation program or a digital circuit, the element data processing unit performs addition processing or averaging processing as the superimposition processing of the plurality of first element data, the second element data is data before phase addition, the first element data and the second element data is having information on element position, depth and signal strength, one of the first element data is data obtained by analog-to-digital converting a plurality of analog element signals that are output from the plurality of elements after the transmitter causes the plurality of elements to transmit the ultrasonic beam once and the plurality of elements receive ultrasonic echoes, the element position indicated by the first element data is a position of the element corresponding to each of the plurality of analog element signals, the depth indicated by the first element data is calculated based on a time from the transmission to the reception of the ultrasonic beam, and the signal strength indicated by the first element data is calculated based on a signal strength of the analog element signal, the transmitter and the receiver transmit and receive ultrasonic waves for a plurality of times and the A/D converter generates a plurality of first element data corresponding to the plurality of transmission and reception, the element data processor generates a plurality of second element data by generating the second element data by changing the first element data of interest a plurality of times, and the element data processing unit includes a first mode that carries out superimposition of the plurality of first element data assuming the ultrasonic beam to be a convergent wave, and, a second mode that carries out superimposition of the plurality of first element data assuming the ultrasonic beam to be a planar wave, and when the distance from the data calculation point to the transmission focal point is greater than the predetermined threshold, the superimposition of the plurality of first element data is carried out in the first mode, and when the distance from the data calculation point to the transmission focal point is equal to or less than the predetermined threshold, the superimposition of the plurality of first element data is carried out in the second mode.

2. The ultrasound inspection device according to claim 1, wherein the calculation point setting unit sets the data calculation point on a transmission line of the ultrasonic beam, and the calculation point positional determination unit determines based on the distance to the transmission focal point on the transmission line corresponding to the data calculation point whether or not the distance to the transmission focal point is equal to or less than a predetermined threshold.

3. The ultrasound inspection device according to claim 1, wherein the transmitter causes the probe to transmit the ultrasonic beam using the plurality of elements in accordance with each of the transmission focal points by changing an element in the center.

4. The ultrasound inspection device according to claim 1, wherein the receiver changes an element in the center of the plurality of elements, the plurality of elements receiving the ultrasonic echoes corresponding to the transmission of the ultrasonic beam by the transmitter.

5. The ultrasound inspection device according to claim 1, wherein the receiver causes the same elements as the plurality of elements used for transmitting the ultrasonic beam by the transmitter to receive the ultrasonic echoes.

6. The ultrasound inspection device according to claim 1, wherein the element data processing unit superimposes the plurality of first element data in accordance with the time the elements received the ultrasonic echoes and the positions of the elements, to generate the second element data corresponding to the data calculation points.

7. The ultrasound inspection device according to claim 1, wherein the element data processing unit includes a delay time calculation unit calculating a delay time for the two or more first element data, and a superimposition processing unit carrying out superimposition of the two or more first element data based on the delay times calculated and the positions of the receiving elements of the probe, to generate the second element data, the delay time calculation unit and the superimposition processing unit are configured by the central processing unit (CPU) and the operation program or the digital circuit, and the delay time calculation unit calculates the delay time assuming the ultrasonic beam to be a convergent wave in the case of the first mode, and calculates the delay time assuming the ultrasonic beam to be a planar wave in the case of the second mode.

8. The ultrasound inspection device according to claim 7, wherein the delay time calculation unit calculates the delay time in the first mode when the distance from the data calculation point to the transmission focal point is equal to or greater than a predetermined first threshold, calculates the delay time in the second mode when the distance from the data calculation point to the transmission focal point is equal to or smaller than a second threshold, the second threshold being smaller than the first threshold, and when the distance from the data calculation point to the transmission focal point is between the first threshold and the second threshold, the delay time is calculated from an average weighted in accordance with the distance to the transmission focal point of the delay time calculated assuming the ultrasonic beam to be a convergent wave and the delay time calculated assuming the ultrasonic beam to be a planar wave.

9. The ultrasound inspection device according to claim 7, wherein the delay time calculation unit calculates the delay time of the two or more first element data based on at least one of information obtained in advance regarding the probe, a velocity of sound in the object to be inspected, a position of the transmission focal point of the ultrasonic beam, a transmission aperture of the probe of the transmitter, and a receiving aperture of the probe of the receiver, and the superimposition processing unit generates the second element data by superimposing the two or more first element data based on a number of first element data to be superimposed from among the two or more first element data and a superimposition processing method, the number of the first element data and the method being set in advance.

10. The ultrasound inspection device according to claim 1, wherein the element data processing unit uses the first element data obtained from transmission of the plurality of ultrasonic beams with different elements in the center.

11. The ultrasound inspection device according to claim 1, wherein the element data processing unit generates the second element data using the first element data obtained from transmission of the plurality of ultrasonic beams with overlapping transmission regions of the ultrasonic beams.

12. The ultrasound inspection device according to claim 1, wherein the element data processing unit superimposes the plurality of first element data obtained from transmission of ultrasonic beams with each element being continuous in a direction of an array of the elements as the element in the center, to generate the second element data.

13. The ultrasound inspection device according to claim 1, wherein the element data processing unit superimposes the plurality of first element data obtained from transmission of ultrasonic beams with the same number of elements on either side of an element in the center as a respective element in the center when transmitting the ultrasonic beam corresponding to the data calculation point, to generate the second element data corresponding to the data calculation point.

14. The ultrasound inspection device according to claim 1, wherein the element data processing unit superimposes the two or more first element data after applying a weighting coefficient to each of the first element data.

15. The ultrasound inspection device according to claim 1, further comprising an element data storage storing all the first element data output by the receiver.

16. An ultrasound image data generation method for generating an ultrasonic beam, inspecting an object to be inspected, and generating ultrasound image data with a probe, the probe including a plurality of elements, the plurality of elements generating each components of the ultrasonic beam, receiving ultrasonic echoes reflected by the object to be inspected, and outputting the received analog element signals, the method comprising:

a focal point setting step of setting a plurality of transmission focal points within the object to be inspected;
a transmission step of causing the probe to generate the ultrasonic beam towards each of the transmission focal points set in the focal point setting step, using the plurality of elements;
a receiving step of receiving the analog element signals received by the plurality of elements corresponding to the transmission of each of the ultrasonic beams towards each of the transmission focal points to perform predetermined processing;
an A/D conversion step of carrying out A/D conversion on the analog element signals processed in the receiving step, to produce first element data being digital element signals;
a calculation point setting step of setting at least one data calculation point within the object to be inspected;
a calculation point positional determination step of determining for each of the data calculation points set in the calculation point setting step whether or not a distance to the transmission focal point is within a predetermined range; and
an element data processing step of acquiring first element data of interest and at least one of first element data in which a central element at the time of ultrasonic beam transmission is different from that of the first element data of interest, shifting the first element data different in central element by an amount of deviation with respect to the central element of the first element data of interest, performing delay time correction on the first element data different in central element, and superimposing the first element data of interest and the first element data different in central element, to generate second element data corresponding to the data calculation point; wherein the element data processing step performs addition processing or averaging processing as the superimposition processing of the plurality of first element data,
the second element data is data before phase addition,
the first element data and the second element data is having information on element position, depth and signal strength,
one of the first element data is data obtained by analog-to-digital converting a plurality of analog element signals that are output from the plurality of elements after the plurality of elements are caused to transmit the ultrasonic beam once in the transmission step and the plurality of elements receive ultrasonic echoes,
the element position indicated by the first element data is a position of the element corresponding to each of the plurality of analog element signals, the depth indicated by the first element data is calculated based on a time from the transmission to the reception of the ultrasonic beam, and the signal strength indicated by the first element data is calculated based on a signal strength of the analog element signal,
the transmission step and the receiving step transmit and receive ultrasonic waves for a plurality of times and the A/D conversion step generates a plurality of first element data corresponding to the plurality of transmission and reception,
the element data processing step generates a plurality of second element data by generating the second element data by changing the first element data of interest a plurality of times, and
the element data processing step includes a first mode carrying out superimposition of the plurality of first element data assuming the ultrasonic beam to be a convergent wave, and, a second mode carrying out superimposition of the plurality of first element data assuming the ultrasonic beam to be a planar wave, and when the distance from the data calculation point to the transmission focal point is greater than a predetermined threshold, the superimposition of the plurality of first element data is carried out in the first mode, and when the distance from the data calculation point to the transmission focal point is equal to or less than the predetermined threshold, the superimposition of the plurality of first elements data is carried out in the second mode.

17. A non-transitory computer-readable recording medium in which is stored an ultrasound image data generation program for causing a computer to execute: generating an ultrasonic beam, inspecting an object to be inspected, and generating ultrasound image data with a probe including a plurality of elements; the plurality of elements generating each components of the ultrasonic beam, receiving ultrasonic echoes reflected by the object to be inspected, and outputting the received analog element signals, the program comprising:

a focal point setting step of setting a plurality of transmission focal points within the object to be inspected;

a transmission step of causing the probe to generate the ultrasonic beam towards each of the transmission focal points set in the focal point setting step, using the plurality of elements;

a receiving step of receiving the analog element signals received by the plurality of elements corresponding to the transmission of each of the ultrasonic beams towards each of the transmission focal points to perform predetermined processing;

an A/D conversion step of carrying out A/D conversion on the analog element signals processed in the receiving step, to produce first element data being digital element signals;

a calculation point setting step of setting at least one data calculation point within the object to be inspected;

a calculation point positional determination step of determining for each of the data calculation points set in the calculation point setting step whether or not a distance to the transmission focal point is within a predetermined range; and an element data processing step of acquiring first element data of interest and at least one of first element data in which a central element at the time of ultrasonic beam transmission is different from that of the first element data of interest, shifting the first element data different in central element by an amount of deviation with respect to the central element of the first element data of interest, performing delay time correction on the first element data different in central element, and superimposing the first element data of interest and the first element data different in central element, to generate second element data corresponding to the data calculation point; wherein the element data processing step performs addition processing or averaging processing as the superimposition processing of the plurality of first element data, the second element data is data before phase addition, the first element data and the second element data is having information on element position, depth and signal strength, one of the first element data is data obtained by analog-to-digital converting a plurality of analog element signals that are output from the plurality of elements after the plurality of elements are caused to transmit the ultrasonic beam once in the transmission step and the plurality of elements receive ultrasonic echoes, the element position indicated by the first element data is a position of the element corresponding to each of the plurality of analog element signals, the depth indicated by the first element data is calculated based on a time from the transmission to the reception of the ultrasonic beam, and the signal strength indicated by the first element data is calculated based on a signal strength of the analog element signal, the transmission step and the receiving step transmit and receive ultrasonic waves for a plurality of times and the A/D conversion step generates a plurality of first element data corresponding to the plurality of transmission and reception, the element data processing step generates a plurality of second element data by generating the second element data by changing the first element data of interest a plurality of times, and the element data processing step includes a first mode carrying out superimposition of the plurality of first element data assuming the ultrasonic beam to be a convergent wave, and, a second mode carrying out superimposition of the plurality of first element data assuming the ultrasonic beam to be a planar wave, and when the distance from the data calculation point to the transmission focal point is greater than a predetermined threshold, the superimposition of the plurality of first element data is carried out in the first mode, and when the distance from the data calculation point to the transmission focal point is equal to or less than the predetermined threshold, the superimposition of the plurality of first elements data is carried out in the second mode.

* * * * *